US012274230B2

(12) United States Patent
Adams et al.

(10) Patent No.: US 12,274,230 B2
(45) Date of Patent: *Apr. 15, 2025

(54) LOW-NICOTINE TOBACCO PLANTS AND TOBACCO PRODUCTS MADE THEREFROM

(71) Applicant: Altria Client Services LLC, Richmond, VA (US)

(72) Inventors: Andrew C. Adams, Midlothian, VA (US); Marcos F. de Godoy Lusso, Chesterfield, VA (US); Sreepriya Pramod, Glen Allen, VA (US); Dongmei Xu, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/321,594

(22) Filed: May 22, 2023

(65) Prior Publication Data

US 2023/0363344 A1 Nov. 16, 2023

Related U.S. Application Data

(60) Continuation of application No. 17/704,650, filed on Mar. 25, 2022, now Pat. No. 11,690,347, which is a division of application No. 16/701,872, filed on Dec. 3, 2019, now Pat. No. 11,317,593.

(60) Provisional application No. 62/775,095, filed on Dec. 4, 2018.

(51) Int. Cl.
*A01H 6/82* (2018.01)
*A01H 5/12* (2018.01)
*A24B 15/10* (2006.01)

(52) U.S. Cl.
CPC .............. *A01H 6/823* (2018.05); *A01H 5/12* (2013.01)

(58) Field of Classification Search
None
See application file for complete search history.

(56) References Cited

U.S. PATENT DOCUMENTS

| | | | |
|---|---|---|---|
| 4,516,590 A | 5/1985 | Teng | |
| 4,528,993 A | 7/1985 | Sensabaugh, Jr. et al. | |
| 4,660,577 A | 4/1987 | Sensabaugh, Jr. et al. | |
| 4,848,373 A | 7/1989 | Lenkey | |
| 4,987,907 A | 1/1991 | Townend | |
| 5,372,149 A | 12/1994 | Roth et al. | |
| 11,317,593 B2 * | 5/2022 | Adams | A24B 15/10 |
| 2005/0178398 A1 | 8/2005 | Breslin et al. | |
| 2006/0191548 A1 | 8/2006 | Strickland et al. | |
| 2008/0245377 A1 | 10/2008 | Marshall et al. | |
| 2012/0216822 A1 | 8/2012 | Lewis et al. | |
| 2012/0222689 A1 | 9/2012 | Xu et al. | |
| 2014/0196730 A1 | 7/2014 | Lewis et al. | |
| 2015/0136152 A1 | 5/2015 | de Godoy Lusso et al. | |
| 2015/0173319 A1 | 6/2015 | Frederick et al. | |
| 2016/0374387 A1 | 12/2016 | Adams et al. | |
| 2017/0233756 A1 | 8/2017 | Begemann et al. | |

FOREIGN PATENT DOCUMENTS

| | | |
|---|---|---|
| CN | 103562393 A | 2/2014 |
| CN | 103687480 A | 3/2014 |
| CN | 105517430 A | 4/2016 |
| CN | 105916392 A | 8/2016 |
| CN | 105960460 A | 9/2016 |
| CN | 108271341 A | 7/2018 |
| WO | WO 2011/027315 | 3/2011 |
| WO | WO 2018/119124 | 6/2018 |

OTHER PUBLICATIONS

U.S. Appl. No. 17/704,650, filed Mar. 25, 2022 which issued as U.S. Pat. No. 11,690,347 on Jul. 4, 2023.
U.S. Appl. No. 16/701,872, filed Dec. 3, 2019 which issued as U.S. Pat. No. 11,317,593 on May 3, 2022.
Bowman et al., "Revised North Carolina Grade Index for Flue-Cured Tobacco," *Tobacco Science*, 32, pp. 39-40 (1988).
Chaplin et al., "Association Between Percent Total Alkaloids and Other Traits in Flue-cured tobacco," *Crop Sci.*, 16, pp. 416-418 (May-Jun. 1976) (Madison, Wisconsin, US).
Chapters 4B and 4C of Tobacco, Production, Chemistry and Technology, Davis & Nielsen, eds., Blackwell Publishing, Oxford (1999), pp. 70-103.
Chen et al., "Unstable Allotetraploid Tobacco Genome due to Frequent Homeologous Recombination, Segmental Deletion, and Chromosome Loss" *Molecular Plant*, 11(7), pp. 914-927 (Jul. 2018) (Cambridge, Massachusetts, US).
Collins et al., "Determination of Nicotine Alkaloids in Tobacco Using the Autoanalyzer," *Tobacco Science*, 13, pp. 79-81 (1969).
Compendium of Tobacco Diseases published by American Phytopathology Society.
"CORESTA Recommended Method No. 7: Determination of Nicotine in the Mainstream Smoke of Cigarettes by Gas Chromatographic Analysis," pp: 1-5, (1987) (updated Aug. 1991) (Paris, France).
Davis et al., "Tobacco, Production, Chemistry and Technology," Blackwell Publishing, Article "Chapters 4B and 4C," pp. 70-103 (1999) (Oxford, England, UK).
"Draft for Diplomatic Conference for the Revision of the International Convention for the Protection of New Varieties of Plants," Mar. 4-19, 1991 (Geneva, Switzerland).
Gaj et al., "ZFN, TALEN and CRISPR/Cas-based Methods for Genome Engineering," *Trends in Biotechnology*, 31(7), pp. 397-405 (Jul. 2013) (Oxford, England, UK).
Hibi et al., "Putrescine N-Methyltransferase in Cultured Roots of *Hyoscyamus albus*," *Plant Physiology*, 100(2), pp. 826-835 (Oct. 1992) (Oxford, England, UK).

(Continued)

*Primary Examiner* — Weihua Fan
(74) *Attorney, Agent, or Firm* — Arnold & Porter Kaye Scholer LLP

(57) ABSTRACT

The present application provides tobacco inbred plants dS1746, dS1746MS, dS1564 and dS1564MS. The present application also provides parts of such plants and products made from those parts. The present application also includes progeny of the provided plants including hybrids.

20 Claims, No Drawings

Specification includes a Sequence Listing.

(56) References Cited

OTHER PUBLICATIONS

International Search Report for International Patent Application No. PCT/US2019/064168 dated Feb. 20, 2020.
Kidd, et al., "The A and B Loci in Tobacco Regulate a Network of Stress Response Genes, Few of Which are Associated with Nicotine Biosynthesis," *Plant Molecular Biology*, 60(5): 699-716 (Mar. 2006) (Baden-Wuerttemberg, Germany).
Legg, "Conventional Breeding for Secondary Products," *Applications of Generic Engineering to Crop Improvement*, 525-533 (1984).
Legg et al., "Inheritance of Percent Total Alkaloids in *Nicotiana-tabacum* L. II. Genetic Effects of Two Loci in Burley x LA Burley 21 Populations," *CA Journal of Genetics and Cytology* 13(2), pp 287-290 (Jun. 1971) (Toronto, CA).
Legg et al., "Registration of LA Burley 21 Tobacco Germplasm," *Crop. Sci.*,10(2), p. 212 (Mar.-Apr. 1970) (Madison, Wisconsin, US).
Miller et al., "A Grade Index for Type 22 and 23 Fire-Cured Tobacco," *Tobacco Intern.*, 192, pp. 55-57 (Dec. 1990) (New York, New York, US).
Miller "Memorandum: Proposed Burley Tobacco Grade Index," Legacy Tobacco Document Library, The University of Tennessee Agricultural Experiment Station (Bates Document #523267826-523267833) (Jul. 1988) (Knoxville, USA).
Official Standard Grades for Burley Tobacco (U.S. Type 31 and Foreign Type 93), effective Nov. 5, 1990 (55 F.R. 40645).
Official Standard Grades for Flue-Cured Tobacco (U.S. Types 11, 12, 13, 14 and Foreign Type 92), effective Mar. 27, 1989 (54 F.R. 7925).
Official Standard Grades for Georgia and Florida Shade-Grown Cigar-Wrapper Tobacco (U.S. Type 62), Effective Apr. 1971.
Official Standard Grades for Ohio Cigar-Leaf Tobacco (U.S. Types 42, 43, and 44), effective Dec. 8, 1963 (28 F.R. 11719 and 28 F.R. 11926).
Official Standard Grades for Pennsylvania Seedleaf Tobacco (U.S. Type 41), effective Jan. 8, 1965 (29 F.R. 16854).
Official Standard Grades for Wisconsin Cigar-Binder Tobacco (U.S. Types 54 and 55), effective Nov. 20, 1969 (34 F.R. 17061).
Shoji, et al., "Clustered Transcription Factor Genes Regulate Nicotine Biosynthesis in Tobacco," *T. Plant Mol. Biol.*, 60 699-716 (2010).
Shoji, et al., "Smoking Out the Masters: Transcriptional Regulators for Nicotine Biosynthesis in Tobacco," *Plant Biotechnology*, 30(3), pp. 217-224 (Sep. 2013) (electronic publication).
Shoji et al., "Clustered Transcription Factor Genes Regulate Nicotine Biosynthesis in Tobacco," *The Plant Cell*, vol. 22, 3390-3409, (Oct. 2010), available online, DOI: 10.1105/tpc. 1 10.078543.
Tso, Chapter 1 in Tobacco, Production, Chemistry and Technology, Davis & Nielsen, eds., Blackwell Publishing, Oxford, England, UK) (1999).
Wernsman, et al., Tobacco. In: Cultivar Development. Crop Species, Chapter Seventeen, W. H. Fehr (ed.), MacMillan Publishing Go., Inc., New York, N.Y. pp. 669-698 (1987).

* cited by examiner

LOW-NICOTINE TOBACCO PLANTS AND TOBACCO PRODUCTS MADE THEREFROM

This application is a Continuation application of U.S. patent application Ser. No. 17/704,650, filed on Mar. 25, 2022, now U.S. Pat. No. 11,690,347, issued on Jul. 4, 2023, which is a Divisional application of U.S. patent application Ser. No. 16/701,872, filed on Dec. 3, 2019, now U.S. Pat. No. 11,317,593, issued on May 3, 2022, which in turn claims benefit under 35 U.S.C. § 119(e) of U.S. Provisional Appln. No. 62/775,095, filed Dec. 4, 2018, herein incorporated by reference in its entirety.

INCORPORATION OF SEQUENCE LISTING

A Sequence Listing conforming to the rules of WIPO Standard ST.26 is hereby incorporated by reference. The Sequence Listing was created on Jul. 14, 2023, and is entitled "P34656US03_ST26.xml," and is 17,942 bytes in size.

FIELD

The present application provides tobacco inbred plants dS1746 (and a male sterile version, dS1746MS), dS1564 (and a male sterile version, dS1564MS), and progenies thereof. The present application also provides parts of such plants and products made from those parts. The present application also includes progeny of the provided plants including hybrids.

BACKGROUND

Tobacco (*Nicotiana tabacum* L.) is an important commercial crop in the United States as well as in other countries. Four major alkaloids are found in tobacco: nicotine, nornicotine, anabasine, and anatabine. Nicotine is the predominant alkaloid, usually accounting for more than 90% of the total alkaloids in commercial tobacco cultivars. Nicotine biosynthesis occurs predominantly in tobacco roots. Tobacco plants then transport nicotine through the vascular bundle to leaves where nicotine is then stored in the vacuoles.

A variety of factors affect tobacco alkaloid levels including genotype, environment, fertilization, and agronomic practices (for example, nicotine production is stimulated by topping, wounding, and herbivore damage). Low-alkaloid traits initially found in strains of Cuban cigar tobacco varieties were introduced into cigarette varieties through a series of backcrosses. Low-alkaloid tobacco germplasm was subsequently registered in the genetic background of cultivar Burley 21 (Legg et al., *Crop Science,* 10:212 (1970)). Genetic studies using the low alkaloid Burley 21 (LA BU21) lines indicated that two unlinked loci contribute to nicotine levels in the tobacco leaf. These two loci are referred to as Nic1 and Nic2. nic1 and nic2 mutations in LA BU21 are semidominant. They show dose-dependent effects on nicotine levels, with the effects of nic1 about 2.4 times stronger than those of nic2. Molecular characterization of Nic2 locus has been reported. The nic2 mutation was shown to contain a deletion of a cluster of transcription factor genes from the ethylene responsive factor (ERF) family (Shoji et al., *Plant Cell,* (10):3390-409 (2010)).

Reducing total alkaloid content in tobacco can have many benefits. Nicotinic alkaloid levels in tobacco plants has been reported to play an important role in protecting plants against insects and herbivores. Consistent with alkaloids' role in insect defense, LA BU21 was reported to be extremely susceptible to insect damage (Legg et al., *Crop Science,* 10:212 (1970)). A further study comparing isogenic lines of flue-cured tobacco with low total alkaloids percentage (approximately 0.20%) with their "normal" recurring parents (total alkaloids 1.85 to 2.70%) reported that yield, grade index, total N, and reducing sugar content in the low alkaloid lines were lower than in the normal flue-cured cultivars (Chaplin and Weeks, *Crop Science,* 16(3):416-18 (1976)).

There is a need to develop tobacco plants and products that contain altered nicotine levels (e.g., reduced nicotine) while maintaining (if not making superior) tobacco leaf quality.

SUMMARY OF THE APPLICATION

In an aspect, the present disclosure provides a seed of tobacco cultivar dS1746 or dS1746MS, a representative sample seed of said cultivar dS1746 having been deposited with the ATCC under ATCC Accession No. PTA-125409, and a representative sample seed of said cultivar dS1746MS having been deposited with the ATCC under ATCC Accession No. PTA-126414.

In another aspect, the present disclosure provides a tobacco plant, or a part thereof, grown from a seed of tobacco cultivar dS1746 or dS1746MS.

In an aspect, the present disclosure provides a harvested leaf of a tobacco plant of tobacco cultivar dS1746 or dS1746MS.

In an aspect, the present disclosure provides a harvested leaf of a tobacco plant of tobacco cultivar dS1746 or dS1746MS, wherein the leaf has a USDA grade index value of 50 or more.

In an aspect, the present disclosure provides a harvested leaf of a tobacco plant of tobacco cultivar dS1746 or dS1746MS, wherein said leaf comprises a nicotine level of less than 0.2% dry weight.

In an aspect, the present disclosure provides cured tobacco comprising tobacco material from a tobacco plant of tobacco cultivar dS1746 or dS1746MS.

In an aspect, the present disclosure provides a tobacco product comprising cured tobacco from a tobacco plant of tobacco cultivar dS1746 or dS1746MS, wherein said product is selected from the group consisting of pipe tobacco, cigar tobacco, cigarette tobacco, chewing tobacco, leaf tobacco, shredded tobacco, and cut tobacco.

In an aspect, the present disclosure provides a tobacco product comprising cured tobacco from a tobacco plant of tobacco cultivar dS1746 or dS1746MS, wherein said tobacco product is selected from the group consisting of a cigarillo, a non-ventilated recess filter cigarette, a vented recess filter cigarette, a cigar, snuff, and chewing tobacco.

In an aspect, the present disclosure provides a tobacco product comprising cured tobacco from a tobacco plant of tobacco cultivar dS1746 or dS1746MS, wherein said product has a nicotine level of less than 0.2% dry weight.

In an aspect, the present disclosure provides a seed of tobacco cultivar dS1564 or dS1564MS, a representative sample seed of said cultivar dS1564 having been deposited with the ATCC under ATCC Accession No. PTA-125408, and a representative sample seed of said cultivar dS1564MS having been deposited with the ATCC under ATCC Accession No. PTA-126413.

In another aspect, the present disclosure provides a tobacco plant, or a part thereof, grown from a seed of tobacco cultivar dS1564 or dS1564MS.

In an aspect, the present disclosure provides a harvested leaf of a tobacco plant of tobacco cultivar dS1564 or dS1564MS.

In an aspect, the present disclosure provides a harvested leaf of a tobacco plant of tobacco cultivar dS1564 or dS1564MS, wherein the leaf has a USDA grade index value of 50 or more.

In an aspect, the present disclosure provides a harvested leaf of a tobacco plant of tobacco cultivar dS1564 or dS1564MS, wherein said leaf comprises a nicotine level of less than 0.2% dry weight.

In an aspect, the present disclosure provides cured tobacco comprising tobacco material from a tobacco plant of tobacco cultivar dS1564 or dS1564MS.

In an aspect, the present disclosure provides a tobacco product comprising cured tobacco from a tobacco plant of tobacco cultivar dS1564 or dS1564MS, wherein said product is selected from the group consisting of pipe tobacco, cigar tobacco, cigarette tobacco, chewing tobacco, leaf tobacco, shredded tobacco, and cut tobacco.

In an aspect, the present disclosure provides a tobacco product comprising cured tobacco from a tobacco plant of tobacco cultivar dS1564 or dS1564MS, wherein said tobacco product is selected from the group consisting of a cigarillo, a non-ventilated recess filter cigarette, a vented recess filter cigarette, a cigar, snuff, and chewing tobacco.

In an aspect, the present disclosure provides a tobacco product comprising cured tobacco from a tobacco plant of tobacco cultivar dS1564 or dS1564MS, wherein said product has a nicotine level of less than 0.2% dry weight.

BRIEF DESCRIPTION OF THE SEQUENCES

SEQ ID NOs: 1 to 5 sets forth nucleotide sequences of five SNP markers used to genotype nic1 or nic2 loci.

SEQ ID NOs: 6 to 10 sets forth nucleotide sequences of low-alkaloid alleles of corresponding SNP markers.

SEQ ID NOs: 11 to 15 sets forth nucleotide sequences of high-alkaloid alleles of corresponding SNP markers.

Various sequences include "N" in nucleotide sequences. "N" can be any nucleotide, e.g., A, T, G, C, or a deletion or insertion of one or more nucleotides. In some instant, a string of "N" are shown. The number of "N" does not necessarily correlate with the actual number of undetermined nucleotides at that position. The actual nucleotide sequences can be longer or shorter than the shown segment of "N".

DETAILED DESCRIPTION OF THE APPLICATION

This description is not intended to be a detailed catalog of all the different ways in which the application may be implemented, or all the features that may be added to the instant application. For example, features illustrated with respect to one embodiment may be incorporated into other embodiments, and features illustrated with respect to a particular embodiment may be deleted from that embodiment. Thus, the application contemplates that in some embodiments of the application, any feature or combination of features set forth herein can be excluded or omitted. In addition, numerous variations and additions to the various embodiments suggested herein will be apparent to those skilled in the art in light of the instant disclosure, which do not depart from the instant application. Hence, the following descriptions are intended to illustrate some particular embodiments of the application, and not to exhaustively specify all permutations, combinations and variations thereof.

Unless otherwise defined, all technical and scientific terms used herein have the same meaning as commonly understood by one of ordinary skill in the art to which this application belongs. The terminology used in the description of the application herein is for the purpose of describing particular embodiments only and is not intended to be limiting of the application.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the application described herein can be used in any combination. Moreover, the present application also contemplates that in some embodiments of the application, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the application and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a nicotine amount or level and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

"Introducing," in the context of a polynucleotide sequence (e.g., a recombinant polynucleotide and/or expression cassette of the application), means presenting a polynucleotide sequence to the plant, plant part, and/or plant cell in such a manner that the polynucleotide sequence gains access to the interior of a cell. Where more than one polynucleotide sequence is to be introduced these polynucleotide sequences can be assembled as part of a single polynucleotide or nucleic acid construct, or as separate polynucleotide or nucleic acid constructs, and can be located on the same or different transformation vectors. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, in some embodiments, a plant cell, plant part or plant of this application can be stably transformed with a recombinant polynucleotide of the application. In other embodiments, a plant cell, plant part or plant of this application can be transiently transformed with a recombinant polynucleotide of the application.

In an aspect, the present application includes a seed of tobacco cultivar dS1746, a representative sample seed of the cultivar having been deposited with the American Type Culture Collection (ATCC) under ATCC Accession No. PTA-125409.

In another aspect, the present application includes a tobacco plant, or part thereof, produced by growing the seed of tobacco cultivar dS1746.

In a further aspect, the present application includes a harvested leaf, or part thereof, of a tobacco plant, or part thereof, produced by growing the seed of tobacco cultivar dS1746.

In an aspect, the present application includes a harvested leaf, or part thereof, of a tobacco plant, produced by growing the seed of tobacco cultivar dS1746, where the leaf has a reduced amount of nicotine relative to a control tobacco variety having a genetic background essentially identical to dS1746 except for the nic1 and nic2 loci introgressed into dS1746 when grown under similar growth conditions.

In a further aspect, the present application includes a tobacco product, prepared from a tobacco plant, or part thereof, produced by growing the seed of tobacco cultivar dS1746, where the product is selected from the group consisting of pipe tobacco, cigar tobacco, cigarette tobacco, chewing tobacco, leaf tobacco, shredded tobacco, cut tobacco and any combination thereof.

In an aspect, the present application includes a tobacco product, prepared from a tobacco plant, or part thereof, produced by growing the seed of tobacco cultivar dS1746, where the product is selected from the group consisting of a cigarillo, a non-ventilated recess filter cigarette, a vented recess filter cigarette, a cigar, snuff, and chewing tobacco.

In another aspect, a tobacco product has a reduced amount of nicotine relative to a tobacco product not prepared from dS1746.

In a further aspect, the present application includes a second tobacco product prepared or produced from a first tobacco product prepared from a tobacco plant, or part thereof, produced by growing the seed of tobacco cultivar dS1746, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In an aspect, the first and second product comprises a reduced amount of nicotine.

In an aspect, the present application includes a part of a tobacco plant, produced by growing the seed of tobacco cultivar dS1746, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present application includes a tissue culture produced from a protoplast or cell from a tobacco plant, or part thereof, produced by growing the seed of tobacco cultivar dS1746, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present application includes a tobacco plant regenerated from a tissue culture produced from a protoplast or cell from a tobacco plant, or part thereof, produced by growing the seed of tobacco cultivar dS1746, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar dS1746.

In an aspect, the present application includes an $F_1$ progeny plant of tobacco cultivar dS1746.

In another aspect, the present application includes an $F_1$ progeny plant of tobacco cultivar dS1746, a representative sample seed of the cultivar having been deposited with the ATCC under ATCC Accession No. PTA-125409, where the $F_1$ plant is male sterile (MS). In a further aspect, an $F_1$ plant is cytoplasmic male sterile (CMS).

In another aspect, the present application includes an $F_1$ progeny seed produced by crossing two tobacco plants and harvesting the resultant tobacco seed, where at least one tobacco plant is a tobacco plant produced by growing the seed of tobacco cultivar dS1746, where at least one tobacco plant is MS or CMS.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1746.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1746, where the plant of tobacco cultivar dS1746 is the male parent.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1746, where the plant of tobacco cultivar dS1746 is the female parent.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1746, where at least one tobacco plant is MS or CMS.

In an aspect, the present application also includes a container of $F_1$ progeny seeds produced by crossing two tobacco plants and harvesting the resultant tobacco seed, where at least one tobacco plant is a tobacco plant produced by growing the seed of tobacco cultivar dS1746, where at least one tobacco plant is MS or CMS.

In an aspect, the present application includes an $F_1$ progeny plant produced by growing a seed produced by crossing two tobacco plants and harvesting the resultant tobacco seed, where at least one tobacco plant is a tobacco plant produced by growing the seed of tobacco cultivar dS1746, and where at least one tobacco plant is MS or CMS.

In an aspect, the present application also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar dS1746, where at least one tobacco plant is MS or CMS. In another aspect, a leaf harvested from an $F_1$ progeny plant has a reduced amount of nicotine relative to a control tobacco variety having a genetic background essentially identical to dS1746 except for the nic1 and nic2 loci introgressed into dS1746 when grown under similar growth conditions.

In an aspect, the present application includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar dS1746, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present application further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar dS1746, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In another aspect, the present application includes a seed of tobacco cultivar dS1746MS, a representative sample seed of the cultivar having been deposited with the ATCC under ATCC Accession No. PTA-126414.

In an aspect, the present application includes a tobacco plant, or part thereof, produced by growing the seed of tobacco cultivar dS1746MS.

In another aspect, the present application includes a harvested leaf, or part thereof, of a tobacco plant, or part thereof, produced by growing the seed of tobacco cultivar dS1746MS.

In another aspect, the present application includes a harvested leaf, or part thereof, of a tobacco plant, produced by growing the seed of tobacco cultivar dS1746MS, where the leaf has a reduced amount of nicotine relative to a control tobacco variety having a genetic background essentially identical to dS1746MS except for the nic1 and nic2 loci introgressed into dS1746MS when grown under similar growth conditions.

In a further aspect, the present application includes a tobacco product, prepared from a tobacco plant, or part thereof, produced by growing the seed of tobacco cultivar dS1746MS, where the product is selected from the group consisting of pipe tobacco, cigar tobacco, cigarette tobacco, chewing tobacco, leaf tobacco, shredded tobacco, cut tobacco and any combination thereof.

In an aspect, the present application includes a tobacco product, prepared from a tobacco plant, or part thereof, produced by growing the seed of tobacco cultivar dS1746MS, where the product is selected from the group consisting of a cigarillo, a non-ventilated recess filter cigarette, a vented recess filter cigarette, a cigar, snuff, and chewing tobacco.

In another aspect, the present application includes a tobacco product, prepared from a tobacco plant, or part thereof, produced by growing the seed of tobacco cultivar dS1746MS, where the product is selected from the group consisting of a cigarillo, a non-ventilated recess filter cigarette, a vented recess filter cigarette, a cigar, snuff, and chewing tobacco, where the product has a reduced amount of nicotine relative a control product prepared from a control tobacco plant having a genetic background essentially identical to dS1746MS except for the nic1 and nic2 loci introgressed into dS1746MS when grown under similar growth conditions.

In a further aspect, the present application includes a second tobacco product prepared or produced from a first tobacco product prepared from a tobacco plant, or part thereof, produced by growing the seed of tobacco cultivar dS1746MS, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In an aspect, the first and/or the second product comprises a reduced amount of nicotine.

In an aspect, the present application includes a part of a tobacco plant, produced by growing the seed of tobacco cultivar dS1746MS, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present application includes a tissue culture produced from a protoplast or cell from a tobacco plant, or part thereof, produced by growing the seed of tobacco cultivar dS1746MS, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present application includes a tobacco plant regenerated from a tissue culture produced from a protoplast or cell from a tobacco plant, or part thereof, produced by growing the seed of tobacco cultivar dS1746MS, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar dS1746MS.

In an aspect, the present application includes an $F_1$ progeny plant of tobacco cultivar dS1746MS.

In another aspect, the present application includes an $F_1$ progeny seed produced by crossing two tobacco plants and harvesting the resultant tobacco seed, where at least one tobacco plant is a plant of tobacco cultivar dS1746MS.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1746MS.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1746MS, where the plant of tobacco cultivar dS1746MS is the female parent.

In another aspect, the present application includes a method for producing a tobacco seed comprising crossing two tobacco plants and harvesting the resultant tobacco seed, where at least one tobacco plant is a plant of tobacco cultivar dS1746MS.

In an aspect, the present application also includes a container of $F_1$ progeny seeds produced by crossing two tobacco plants and harvesting the resultant tobacco seed, where at least one tobacco plant is a tobacco plant produced by growing the seed of tobacco cultivar dS1746MS.

In an aspect, the present application includes an $F_1$ progeny plant produced by growing a seed produced by crossing two tobacco plants and harvesting the resultant tobacco seed, where at least one tobacco plant is a tobacco plant produced by growing the seed of tobacco cultivar dS1746MS.

In an aspect, the present application also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar dS1746MS.

In another aspect, the present application further includes a harvested leaf of an $F_1$ progeny plant having a reduced amount of nicotine produced by growing a seed produced by crossing two tobacco plants and harvesting the resultant tobacco seed, where at least one tobacco plant is a tobacco plant produced by growing the seed of tobacco cultivar dS1746MS.

In an aspect, the present application includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is a tobacco plant produced by growing the seed of tobacco cultivar dS1746MS, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present application further includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is a tobacco plant produced by growing the seed of tobacco cultivar dS1746MS, and where the tobacco product is selected from the group consisting of a cigarillo, a non-ventilated recess filter cigarette, a vented recess filter cigarette, a cigar, snuff, and chewing tobacco.

In an aspect, the present application further includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is a tobacco plant produced by growing the seed of tobacco cultivar dS1746MS, and where the tobacco product is selected from the group consisting of a cigarillo, a non-ventilated recess filter cigarette, a vented recess filter cigarette, a cigar, snuff, and chewing tobacco, and further where the product has a reduced amount of nicotine.

In an aspect, the present application includes a method for producing a tobacco seed comprising crossing two tobacco plants and harvesting the resultant tobacco seed, where at least one tobacco plant is a plant of tobacco cultivar dS1746MS.

In an aspect, the present application includes a method of vegetatively propagating a plant of a tobacco cultivar comprising the steps of (a) collecting tissue capable of being propagated from a plant of a tobacco cultivar dS1746 or dS1746MS; (b) cultivating the tissue to obtain a proliferated shoot; and (c) rooting the proliferated shoots to obtain a rooted plantlet.

In an aspect, the present application includes a method of vegetatively propagating a plant of a tobacco cultivar comprising the steps of (a) collecting tissue capable of being propagated from a plant of a tobacco cultivar dS1746 or dS1746MS; (b) cultivating the tissue to obtain a proliferated shoot; (c) rooting the proliferated shoots to obtain a rooted plantlet; and (d) growing a plant from the rooted plantlet.

In an aspect, the present application includes a method of introducing a desired trait into a tobacco cultivar comprising: (a) crossing a plant of a first tobacco cultivar dS1746 or dS1746MS, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar; and (e) repeating steps (c) and (d) three or more times (e.g., 3, 4, 5, 6, 7, 8, 9, 10, and the like) in succession to produce selected fourth or higher backcross progeny that comprise the desired trait. In an aspect, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present application includes a method of introducing a desired trait into a tobacco cultivar comprising: (a) crossing a plant of a first tobacco cultivar dS1746, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar dS1746 to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar dS1746; and (e) repeating steps (c) and (d) three or more times in succession to produce selected fourth or higher backcross progeny that comprise the desired trait, where the trait is cytoplasmic male sterility (CMS). In an aspect, steps (c) and (d) can be repeated one or more times in succession to produce second or higher backcross progeny comprising the desired trait, where the trait is CMS.

In an aspect, the present application includes a method of introducing a desired trait into a tobacco cultivar comprising: (a) crossing a plant of a first tobacco cultivar dS1746, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar to produce a backcross $BC_1F_1$ progeny seed; (d) growing the $BC_1F_1$ progeny seed and selecting a backcross $BC_1F_1$ progeny plant comprising the desired trait and the physiological and essentially all of morphological characteristics of the first tobacco cultivar; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In an aspect, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present application includes a method of introducing a desired trait into a tobacco cultivar comprising: (a) crossing a plant of a first tobacco cultivar dS1746 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar, dS1746 to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar dS1746; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is dS1746MS. In an aspect, steps (c) and (d) can be repeated one or more times in succession to produce second or higher backcross progeny comprising the desired trait, where the trait is CMS and the CMS trait is obtained from the cytoplasm of *Nicotiana suaveolens*.

In an aspect, the present application includes a tobacco plant produced by a method comprising introducing a desired trait into a tobacco cultivar comprising: (a) crossing a plant of a first tobacco cultivar dS1746 or dS1746MS, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar dS1746 or dS1746MS to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar dS1746 or dS1746MS; and (e) repeating steps (c) and (d) three or more times in succession to produce selected fourth or higher backcross progeny that comprise the desired trait. In an aspect, steps (c) and (d) can be repeated one or more times in succession to produce second or higher backcross progeny that comprise the desired trait.

In another aspect, the present application includes a method of introducing a desired trait into a tobacco cultivar comprising: (a) crossing a plant of a first tobacco cultivar dS1746 or dS1746MS with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar dS1746 or dS1746MS to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, dS1746 or dS1746MS; and (e) repeating steps (c) and (d) one or more times in succession to produce a selected second, third, fourth or higher backcross progeny plant that comprises the desired trait and essentially all of the physiological and morphological characteristics of the first tobacco cultivar, dS1746 or dS1746MS.

In another aspect, the present application includes a method of introducing a desired trait into a tobacco cultivar comprising: (a) crossing a plant of a first tobacco cultivar dS1746 or dS1746MS, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an F1 progeny seed; (b) growing the F1 progeny seed into an F1 progeny plant and selecting the F1 progeny plant having the desired trait; (c) crossing the selected F1 progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, dS1746 or dS1746MS; and (e) repeating steps (c) and (d) one or more times in succession to produce a selected second, third, fourth or higher backcross progeny plant that comprises the desired trait and essentially all of the physiological and morphological characteristics of the first tobacco cultivar, dS1746 or dS1746MS.

In another aspect, the present application includes a method of introducing a desired trait into a tobacco cultivar comprising: (a) crossing a plant of a first tobacco cultivar dS1746 or dS1746MS, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an F1 progeny seed; (b) growing the F1 progeny seed into an F1 progeny plant and selecting the F1 progeny plant having the desired trait; (c) crossing the selected F1 progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, dS1746 or dS1746MS; and (e) repeating steps (c) and (d) one or more times in succession to produce a selected second, third, fourth or higher backcross progeny plant that comprises the desired trait and essentially all of the physiological and morphological characteristics of the first tobacco cultivar, dS1746 or dS1746MS, where the plant has a desired trait of disease resistance.

In another aspect, the present application includes a method for producing a tobacco plant comprising: identifying a first tobacco plant comprising a nucleotide sequence selected from the group consisting of SEQ ID NOs: 6 to 10, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence. In an aspect, the second tobacco plant comprises a nucleotide sequence selected from the group consisting of SEQ ID NOs: 6 to 10, and any combination thereof. In a further aspect, the third tobacco plant comprises a nucleotide sequence selected from the group consisting of SEQ ID NOs: 6 to 10, and any combination thereof. In an aspect, the first tobacco plant is a plant of tobacco cultivar dS1746 or dS1746MS. In another aspect, the second tobacco plant is a plant of tobacco cultivar dS1746 or dS1746MS. In a further aspect, the third tobacco plant is a plant of tobacco cultivar dS1746 or dS1746MS.

In another aspect, the present application includes a method of producing a plant of tobacco cultivar dS1746 or dS1746MS comprising at least one (e.g., 1, 2, 3, 4, 5, 6, 7, 8, and the like) additional desired trait comprising the steps of: (a) collecting tissue capable of being propagated from a plant of tobacco cultivar dS1746 or dS1746MS; and (b) introducing at least one transgene (nucleic acid construct) conferring at least one desired trait into the tissue.

In another aspect, the present application includes a method of producing an herbicide resistant tobacco plant comprising transforming a tobacco plant, or part thereof, produced by growing a seed of tobacco cultivar dS1746 or dS1746MS with at least one transgene (nucleic acid construct), where the at least one transgene (nucleic acid construct) confers resistance to an herbicide. In a further aspect, an herbicide is selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present application includes an herbicide resistant tobacco plant produced by a method comprising transforming a tobacco plant, or part thereof, produced by growing a seed of tobacco cultivar dS1746 or dS1746MS with at least one transgene (nucleic acid construct), where the at least one transgene (nucleic acid construct) confers resistance to an herbicide. In a further aspect, an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present application includes a method of producing a pest and/or insect resistant tobacco plant where the method comprises transforming a tobacco plant produced by growing a seed of tobacco cultivar dS1746 or dS1746MS, with at least one transgene (nucleic acid construct) that confers pest and/or insect resistance.

In a further aspect, the present application includes a pest and/or insect resistant tobacco plant produced by a method comprising transforming a tobacco plant produced by growing a seed of tobacco cultivar dS1746 or dS1746MS, with at least one transgene (nucleic acid construct) that confers pest and/or insect resistance.

In a further aspect, the present application includes a pest and/or insect resistant tobacco plant produced by a method comprising transforming a tobacco plant produced by growing a seed of tobacco cultivar dS1746 or dS1746MS, with at least one transgene (nucleic acid construct) that confers pest and/or insect resistance, where the transgene (nucleic acid construct) encodes a *Bacillus thuringiensis* (BT) endotoxin.

In another aspect, the present application includes a method of producing a disease resistant tobacco plant, the method comprising transforming a tobacco plant produced by growing a seed of tobacco cultivar dS1746 or dS1746MS with at least one transgene (nucleic acid construct) that confers disease resistance.

In a further aspect, the present application includes a disease resistant tobacco plant produced by transforming a tobacco plant produced by growing a seed of tobacco cultivar dS1746 or dS1746MS with at least one transgene (nucleic acid construct) that confers disease resistance.

As used herein, "similar growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine. Minor tobacco alkaloids include nicotine-n-oxide, N-methyl anatabine, N-methyl anabasine, pseudooxynicotine, 2,3 dipyridyl and others.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E. See also Hibi et al., *Plant Physiology* 100: 826-35 (1992) for a method using gas-liquid chromatography equipped with a capillary column and an FID detector.

Alternatively, tobacco total alkaloids can be measured using a segmented-flow colorimetric method developed for analysis of tobacco samples as adapted by Skalar Instrument Co (West Chester, PA) and described by Collins et al., *Tobacco Science* 13:79-81 (1969). In short, samples of tobacco are dried, ground, and extracted prior to analysis of total alkaloids and reducing sugars. The method then employs an acetic acid/methanol/water extraction and charcoal for decolorization. Determination of total alkaloids was based on the reaction of cyanogen chloride with nicotine alkaloids in the presence of an aromatic amine to form a colored complex which is measured at 460 nm. Unless specified otherwise, total alkaloid levels or nicotine levels shown herein are on a dry weight basis (e.g., percent total alkaloid or percent nicotine).

In an aspect, tobacco plants provided herein comprise an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, tobacco plants provided herein comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, tobacco plants provided herein comprise an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides tobacco plants having altered nicotine levels without negative impacts over other tobacco traits, e.g., leaf grade index value. In an aspect, a low-nicotine or nicotine-free tobacco variety provides cured tobacco of commercially acceptable grade. Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40(1988); Legacy Tobacco Document Library (Bates Document #523267826-523267833, Jul. 1, 1988, Memorandum on the Proposed Burley Tobacco Grade Index); and Miller et al., 1990, *Tobacco Intern.,* 192:55-57 (all foregoing references are incorporated by inference in their entirety). In an aspect, a USDA grade index is a 0-100 numerical representation of federal grade received and is a weighted average of all stalk positions. A higher grade index indicates higher quality. Alternatively, leaf grade can be determined via hyperspectral imaging. See e.g., WO 2011/027315 (published on Mar. 10, 2011, and incorporated by inference in its entirety).

dS1746

In an aspect, the present application provides tobacco cultivars, and parts thereof, grown or developed from dS1746. In another aspect, the present application provides a tobacco plant, or part thereof, produced by growing a seed of dS1746. In a further aspect, a plant of the present application can include a plant with all, or essentially all, of the morphological and physiological characteristics of cultivar dS1746.

While not being limited by process, dS1746 is a backcross-derived version of burley tobacco cultivar TN 90 carrying homozygous introgressions at two loci (nic1 and nic2 loci), which introgressions result in an overall reduction of alkaloid content in the line. dS1746 is the result of three backcrosses with burley cultivar TN90 as the recurrent parent, followed by four rounds of selfing with selection for homozygosity for nic1 and nic2 loci. dS1746 progeny plants have genetic backgrounds that are at least 95%, at least 97%, at least 98%, or at least 99% similar to TN90. dS1746 plants exhibit low nicotine levels.

dS1746MS

In an aspect, the present application provides tobacco cultivars, and parts thereof, grown or developed from dS1746MS. In a further aspect, the present application also includes a tobacco plant, or part thereof, produced by growing a seed of dS1746MS. In a still further aspect, a plant of the present application can include a plant with all, or essentially all, of the morphological and physiological characteristics of cultivar dS1746MS. dS1746MS is a male-sterile (MS) version of dS1746. Because the dS1746MS line is male sterile, it is maintained via pollination with dS1746. dS1746 is crossed as the male parent to dS1746MS to prepare dS1746MS $F_1$ progeny plants. dS1746MS progeny plants can have genetic backgrounds that are at least 95%, at least 97%, at least 98%, or at least 99% similar to TN90. dS1746MS and dS1746MS $F_1$ progeny plants exhibit low nicotine levels.

Other Plants

The present application includes a tobacco seed produced by crossing two parent tobacco plants and harvesting the resultant tobacco seed, where at least one parent tobacco plant is dS1746. In one aspect, the dS1746 is the male parent plant. In another aspect, the dS1746MS is the female parent plant. One aspect of the present application provides tobacco plants that are homozygous at the nic1 and nic2 loci, and which share a genetic background that is greater than about 75%, 80%, 85%, 90%, 95%, 98%, or 99% similar to TN90 or MS TN90 (male sterile TN90). In one aspect, approximately or greater than about 50%, 75%, or 100% of a progeny's genetics is provided by a plant of the present application that is homozygous at the nic1 and nic2 loci. In one aspect, a plant of the present application has a genetic background that is at least 95%, at least 97%, at least 98%, or at least 99% similar to TN90 or MS TN90. In another aspect, a plant of the present application exhibits low nicotine. In one aspect, a plant of the present application is the progeny plant of a female or male parent plant that is *Fusarium* wilt resistant. In another aspect, a plant of dS1746 has low resistance to black shank and moderate resistance to bacterial wilt.

In an aspect, a plant of the present application is a medium-late maturing variety with moderately high yield potential. In another aspect, a plant of the present application offers a broad range of important agronomic characteristics. In a further aspect, a plant of the present application has one, two, three, four or more of the traits including moderate resistance to black shank, some tolerance to blue mold, black root rot resistance, and resistance to common virus diseases. In another aspect, a plant of the present application has blue mold tolerance and level 4 resistance to both races of black shank and high root rot resistance. In an aspect, a plant of the present application, such as dS1746, dS1746MS, dS1564 or dS1564MS, lacks *Fusarium* wilt resistance. In another aspect, a plant of the present application is *Fusarium* wilt resistant. In another aspect, a plant of the present application has low resistance to black shank and moderate resistance to bacterial wilt.

In an aspect, a tobacco plant of the present application comprises one or more mutations (e.g., null or loss-of-function mutations) in one or more nicotine demethylase genes (CYP82E4, CYP82E5v2, CYP85E10). In another aspect, a tobacco plant comprises one or more of cyp82e4 W329Stop, cyp82e5v2 W422Stop, and cyp82e10 P381S mutations.

In an aspect, the plants of the present application have reduced or eliminated ability to convert nicotine to nornicotine. In an aspect, the percentage nicotine conversion can be less than about 75%, 70%, 60%, 50%, or 25% of that found in TN90 or K326. In another aspect, the nicotine conversion in plants of the present application, including dS1746, dS1746MS, dS1564 or dS1564MS, can be less than about 4%, about 3.5%, about 3%, about 2.5%, about 2%, about 1.5%, about 1%, or any range therein. In a still other aspect, the nicotine conversion in plants of the present application, including dS1746, dS1746MS, dS1564 or dS1564MS, can be in a range from about 3% to about 1%, about 3% to about 0.5%, or about 2% to about 0.5%. In an aspect, the tobacco plants of the present application can have a nicotine conversion rate of about 3.5, 3.25, 3.0 or 2.75% or less. In another aspect, the nicotine conversion rate of tobacco plants of the present application can be about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5% or less or any range therein. In another aspect, the nicotine conversion rate of tobacco plants of the present application can be about 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6% or less or any range therein. In another aspect, the nicotine conversion rates can be in a range from about 0.5% to about 0.9%, about 0.5% to about 1.5%, about 0.5% to about 2.0%, about 0.5% to about 2.5%, about 0.5% to about 2.75%, and about 0.5% to about 3.0%. In another aspect, the nicotine conversion rates can be in a range from about 1.0% to about 1.5%, about 1.0% to about 1.75%, about 1.0% to about 2.0%, about 1.0% to about 2.5%, about 1.0% to about 2.75%, or about 1.0% to about 3.0%. In another aspect, the nicotine conversion rate in a plant of the present application can be less than about 2.9, 2.75, 2.5, 2.25, 2.0, 1.9, 1.8, 1.7, 1.6, 1.5, 1.4, 1.3, 1.2, 1.1 or 1.0% or any range therein.

In another aspect, the tobacco plants of the present application typically have a reduced amount of nornicotine of less than about 0.10% dry weight. For example, the nornicotine content in such plants can be about 1.2, 1.0, 0.7, 0.5, 0.4, 0.2, 0.1, 0.09, 0.085, 0.08, 0.075, 0.07, 0.065, 0.06, 0.055, 0.05, 0.045, 0.04, 0.035, 0.025, 0.01, 0.009, 0.0075, 0.005, 0.0025, 0.001, 0.0009, 0.00075, 0.0005, 0.00025, or 0.0001% dry weight, or undetectable, or any range therein. In another aspect, the nornicotine content can be less than about 1.2, 1.0, 0.9, 0.8, 0.7, 0.5, 0.4, 0.2, 0.1, 0.075, 0.05, 0.025, 0.01, 0.009, 0.0075, 0.005, 0.0025, 0.001, 0.0009, 0.00075, 0.0005, 0.00025, or 0.0001% dry weight, or any range therein. In another aspect, the nornicotine content in such plants can be in a range from about 1.2% to about 1.0%, about 0.7% to about 0.5%, about 0.4% to about 0.2%, about 0.1% to about 0.075%, about 0.05% to about 0.025%, about 0.01% to about 0.0075%, about 0.005% to about 0.0025%, about 0.001% to about 0.00075%, about 0.0005% to about 0.00025%, or about 0.0005% to about 0.0001% dry weight.

In an aspect, in a plant of the present application, the nornicotine is a relatively small percentage of total alkaloids in the plant compared to a commercial seedlot of TN90 or K326. In an aspect, the nornicotine in a plant of the present application can be about 2% to about 1%, less than 3%, about 2%, about 1.5%, about 1%, or 0.75% of total alkaloids. Tobacco products having a reduced amount of nitrosamine content can be manufactured using tobacco plant material from plants and plant parts of the present application. Thus, in some embodiments, a tobacco product manufactured using tobacco plant material from plants and plant parts of the present application can comprise a reduced amount of nornicotine of less than about 3 mg/g. For example, the nornicotine content in such a product can be 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 5 µg/g, 1 µg/g, 750 ng/g, 500 ng/g, 250 ng/g, 100 ng/g, 75 ng/g, 50 ng/g, 25 ng/g, 10 ng/g, 5 ng/g, 1 ng/g, 750 pg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and the like, or undetectable, or any range therein. The tobacco product typically has a reduced amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and the like, or undetectable, or any range therein.

Differences between two inbred tobacco varieties or two hybrid tobacco varieties can be evaluated using statistical approaches. Statistical analysis includes the calculation of mean values, determination of the statistical significance of the sources of variation, and the calculation of the appropriate variance components. Methods for determining statistical significance are known in the art. Statistical software is available, for example, the PROC GLM function of SAS. Significance is generally presented as a "p-value." A statistically significant p-value is less than 0.10. In a preferred aspect, the p-value is less than or equal to 0.05. In another aspect, the p-value is 0.04 or less, 0.03 or less, or 0.02 or less. In yet another aspect, a statistically significant value is less than 0.01. In yet another aspect, it can be less than 0.009, less than 0.008, less than 0.007, less than 0.006, less than 0.005, less than 0.004, less than 0.003, less than 0.002, or less than 0.001.

In an aspect, the tobacco plants of the present application have a USDA leaf quality index of at least about 85, 80, 75, 73, 72, 71, 70, 69, 68, 67 or 66 or any range therein. In an aspect, the tobacco plants of the present application have a USDA leaf quality index of at least about 65. In another aspect, the quality index may be at least about 55, 60, 62.5, or any range therein. In another aspect, tobacco plants of the present application can have a leaf quality index in the range of about 60 to about 65, about 60 to about 70, about 62.5 to about 65, about 62.5 to about 70, or about 65 to about 70.

A plant of the present application, including dS1746, dS1746MS, dS1564, dS1564MS, or a progeny thereof, can have any yield potential, including high (e.g., over 3000 lbs/A), moderately high (e.g., 2200-3000 lbs/A), and moderate (e.g., less than 2000 lbs/A) yield potential.

An aspect of the present application provides for parts of cultivar dS1746, dS1746MS, dS1564 or dS1564MS. A part of a cultivar can comprise any plant part and includes, but is not limited to, leaves, pollen, embryos, cotyledons, hypocotyls, roots, root tips, anthers, flowers, ovules, shoots, stems, stalks, pith and capsules, tissue culture comprising tissue, callus, cells or protoplasts of cultivar dS1746, dS1746MS, dS1564 or dS1564MS. In another aspect, the present application provides for parts from hybrids derived from cultivar dS1746 or dS1746MS. In yet another aspect, the present application provides for parts from genetically modified (e.g., by conventional breeding or genetic engineering techniques) forms of the foregoing plants and tissue culture.

An additional aspect of the present application provides products comprising tobacco from the plants of the present application, and parts thereof. Another aspect of the application provides cured plant parts, which include, but are not limited to, a leaf, pollen, ovule, embryo, cotyledon, hypocotyl, meristematic cell, protoplast, root, root tip, pistil, anther, flower, shoot, stem, pod, petiole, and the like, and combinations thereof.

Thus, in an aspect, the present application provides a cured tobacco comprising the leaves of the tobacco plant designated dS1746. In another aspect, the present application provides a cured tobacco comprising the leaves of the tobacco plant designated dS1746MS.

In an aspect, the present application provides a cured tobacco comprising the stems of the tobacco plant designated dS1746. In another aspect, the present application provides a cured tobacco comprising the stems of the tobacco plant designated dS1746MS.

In an aspect, the present application provides a cured tobacco comprising the leaves and stems of the tobacco plants designated dS1746. In another aspect, the present application provides a cured tobacco comprising the leaves and stems of the tobacco plants designated dS1746MS.

The present application also provides a container of dS1746 or dS1746MS seeds or other seeds of the present application in which alkaloids obtained from tobacco plants grown from greater than about 50% of the seeds have decreased nicotine. In another aspect, alkaloids obtained from dS1746 or dS1746MS plants or other plants of the present application grown from greater than about 55%, 60%, 65%, 70%, 75%, 80%, 85%, 90%, or 95% of the seeds in the container have decreased nicotine.

The container of dS1746 or dS1746MS seeds or other seeds of the present application may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds.

Containers of dS1746 or dS1746MS seeds or other seeds of the present application may be any container available in the art. By way of a non-limiting example, a container may be a box, a bag, a packet, a pouch, a tape roll, a pail, a foil, or a tube.

In another aspect, the present application also provides a container of dS1746 or dS1746MS in which greater than about 50% of dS1746 or dS1746MS seeds or other seeds of the present application have decreased nicotine.

In an aspect, also provided are populations of tobacco plants described. In an aspect, a population of tobacco plants has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants is in a soil type with low to medium fertility.

In one aspect, the present application provides a seed of a dS1746 or dS1746MS plant or other plant of the present application in which a plant grown from said seed is male sterile.

In an aspect, the present application includes a seed of tobacco cultivar dS1564, a representative sample seed of the cultivar having been deposited with the American Type Culture Collection (ATCC) under ATCC Accession No. PTA-125408.

In another aspect, the present application includes a tobacco plant, or part thereof, produced by growing the seed of tobacco cultivar dS1564.

In a further aspect, the present application includes a harvested leaf, or part thereof, of a tobacco plant, or part thereof, produced by growing the seed of tobacco cultivar dS1564.

In an aspect, the present application includes a harvested leaf, or part thereof, of a tobacco plant, produced by growing the seed of tobacco cultivar dS1564, where the leaf has a reduced amount of nicotine relative to a control tobacco variety having a genetic background essentially identical to dS1564 except for the nic1 and nic2 loci introgressed into dS1564 when grown under similar growth conditions.

In a further aspect, the present application includes a tobacco product, prepared from a tobacco plant, or part thereof, produced by growing the seed of tobacco cultivar dS1564, where the product is selected from the group consisting of pipe tobacco, cigar tobacco, cigarette tobacco, chewing tobacco, leaf tobacco, shredded tobacco, cut tobacco and any combination thereof.

In an aspect, the present application includes a tobacco product, prepared from a tobacco plant, or part thereof, produced by growing the seed of tobacco cultivar dS1564, where the product is selected from the group consisting of a cigarillo, a non-ventilated recess filter cigarette, a vented recess filter cigarette, a cigar, snuff, and chewing tobacco.

In another aspect, a tobacco product has a reduced amount of nicotine relative to a tobacco product not prepared from dS1564.

In a further aspect, the present application includes a second tobacco product prepared or produced from a first tobacco product prepared from a tobacco plant, or part thereof, produced by growing the seed of tobacco cultivar dS1564, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In an aspect, the first and second product comprises a reduced amount of nicotine.

In an aspect, the present application includes a part of a tobacco plant, produced by growing the seed of tobacco cultivar dS1564, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present application includes a tissue culture produced from a protoplast or cell from a tobacco plant, or part thereof, produced by growing the seed of tobacco cultivar dS1564, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present application includes a tobacco plant regenerated from a tissue culture produced from a protoplast or cell from a tobacco plant, or part thereof, produced by growing the seed of tobacco cultivar dS1564, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar dS1564.

In an aspect, the present application includes an $F_1$ progeny plant of tobacco cultivar dS1564.

In another aspect, the present application includes an $F_1$ progeny plant of tobacco cultivar dS1564, a representative sample seed of the cultivar having been deposited with the ATCC under ATCC Accession No. PTA-125408, where the $F_1$ plant is male sterile (MS). In a further aspect, an $F_1$ plant is cytoplasmic male sterile (CMS).

In another aspect, the present application includes an $F_1$ progeny seed produced by crossing two tobacco plants and harvesting the resultant tobacco seed, where at least one tobacco plant is a tobacco plant produced by growing the seed of tobacco cultivar dS1564, where at least one tobacco plant is MS or CMS.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1564.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1564, where the plant of tobacco cultivar dS1564 is the male parent.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1564, where the plant of tobacco cultivar dS1564 is the female parent.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1564, where at least one tobacco plant is MS or CMS.

In an aspect, the present application also includes a container of $F_1$ progeny seeds produced by crossing two tobacco plants and harvesting the resultant tobacco seed, where at least one tobacco plant is a tobacco plant produced by growing the seed of tobacco cultivar dS1564, where at least one tobacco plant is MS or CMS.

In an aspect, the present application includes an $F_1$ progeny plant produced by growing a seed produced by crossing two tobacco plants and harvesting the resultant tobacco seed, where at least one tobacco plant is a tobacco plant produced by growing the seed of tobacco cultivar dS1564, and where at least one tobacco plant is MS or CMS.

In an aspect, the present application also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar dS1564, where at least one tobacco plant is MS or CMS. In another aspect, a leaf harvested from an $F_1$ progeny plant has a reduced amount of nicotine relative to a control tobacco variety having a genetic background essentially identical to dS1564 except for the nic1 and nic2 loci introgressed into dS1564 when grown under similar growth conditions.

In an aspect, the present application includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar dS1564, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present application further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar dS1564, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In another aspect, the present application includes a seed of tobacco cultivar dS1564MS, a representative sample seed of the cultivar having been deposited with the ATCC under ATCC Accession No. PTA-126413.

In an aspect, the present application includes a tobacco plant, or part thereof, produced by growing the seed of tobacco cultivar dS1564MS.

In another aspect, the present application includes a harvested leaf, or part thereof, of a tobacco plant, or part thereof, produced by growing the seed of tobacco cultivar dS1564MS.

In an aspect, the present application includes a harvested leaf, or part thereof, of a tobacco plant, produced by growing the seed of tobacco cultivar dS1564MS, where the leaf has a reduced amount of nicotine relative to a control tobacco variety having a genetic background essentially identical to dS1564MS except for the nic1 and nic2 loci introgressed into dS1564MS when grown under similar growth conditions.

In a further aspect, the present application includes a tobacco product, prepared from a tobacco plant, or part thereof, produced by growing the seed of tobacco cultivar dS1564MS, where the product is selected from the group consisting of pipe tobacco, cigar tobacco, cigarette tobacco, chewing tobacco, leaf tobacco, shredded tobacco, cut tobacco and any combination thereof.

In an aspect, the present application includes a tobacco product, prepared from a tobacco plant, or part thereof, produced by growing the seed of tobacco cultivar dS1564MS, where the product is selected from the group consisting of a cigarillo, a non-ventilated recess filter cigarette, a vented recess filter cigarette, a cigar, snuff, and chewing tobacco.

In another aspect, the present application includes a tobacco product, prepared from a tobacco plant, or part thereof, produced by growing the seed of tobacco cultivar dS1564MS, where the product is selected from the group consisting of a cigarillo, a non-ventilated recess filter cigarette, a vented recess filter cigarette, a cigar, snuff, and chewing tobacco, where the product has a reduced amount of nicotine relative a control product prepared from a control tobacco plant having a genetic background essentially identical to dS1564MS except for the nic1 and nic2 loci introgressed into dS1564MS when grown under similar growth conditions.

In a further aspect, the present application includes a second tobacco product prepared or produced from a first tobacco product prepared from a tobacco plant, or part thereof, produced by growing the seed of tobacco cultivar dS1564MS, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In an aspect, the first and/or the second product comprises a reduced amount of nicotine.

In an aspect, the present application includes a part of a tobacco plant, produced by growing the seed of tobacco cultivar dS1564MS, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present application includes a tissue culture produced from a protoplast or cell from a tobacco plant, or part thereof, produced by growing the seed of tobacco cultivar dS1564MS, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present application includes a tobacco plant regenerated from a tissue culture produced from a protoplast or cell from a tobacco plant, or part thereof, produced by growing the seed of tobacco cultivar dS1564MS, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar dS1564MS.

In an aspect, the present application includes an $F_1$ progeny plant of tobacco cultivar dS1564MS.

In another aspect, the present application includes an $F_1$ progeny seed produced by crossing two tobacco plants and harvesting the resultant tobacco seed, where at least one tobacco plant is a plant of tobacco cultivar dS1564MS.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1564MS.

In another aspect, the present application includes a method for producing a tobacco seed comprising crossing two tobacco plants and harvesting the resultant tobacco seed, where at least one tobacco plant is a tobacco plant produced by growing the seed of tobacco cultivar dS1564MS, where the plant of tobacco cultivar dS1564MS is the female parent.

In another aspect, the present application includes a method for producing a tobacco seed comprising crossing two tobacco plants and harvesting the resultant tobacco seed, where at least one tobacco plant is a plant of tobacco cultivar dS1564MS.

In an aspect, the present application also includes a container of $F_1$ progeny seeds produced by crossing two tobacco plants and harvesting the resultant tobacco seed, where at least one tobacco plant is a tobacco plant produced by growing the seed of tobacco cultivar dS1564MS.

In an aspect, the present application includes an $F_1$ progeny plant produced by growing a seed produced by crossing two tobacco plants and harvesting the resultant tobacco seed, where at least one tobacco plant is a tobacco plant produced by growing the seed of tobacco cultivar dS1564MS.

In an aspect, the present application also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar dS1564MS.

In another aspect, the present application further includes a harvested leaf of an $F_1$ progeny plant having a reduced amount of nicotine produced by growing a seed produced by crossing two tobacco plants and harvesting the resultant tobacco seed, where at least one tobacco plant is a tobacco plant produced by growing the seed of tobacco cultivar dS1564MS.

In an aspect, the present application includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is a tobacco plant produced by growing the seed of tobacco cultivar dS1564MS, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present application further includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is a tobacco plant produced by growing the seed of tobacco cultivar dS1564MS, and where the tobacco product is selected from the group consisting of a cigarillo, a non-ventilated recess filter cigarette, a vented recess filter cigarette, a cigar, snuff, and chewing tobacco.

In an aspect, the present application further includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is a tobacco plant produced by growing the seed of tobacco cultivar dS1564MS, and where the tobacco product is selected from the group consisting of a cigarillo, a non-ventilated recess filter cigarette, a vented recess filter cigarette, a cigar, snuff, and chewing tobacco, and further where the product has a reduced amount of nicotine.

In an aspect, the present application includes a method for producing a tobacco seed comprising crossing two tobacco plants and harvesting the resultant tobacco seed, where at least one tobacco plant is a plant of tobacco cultivar dS1564MS.

In an aspect, the present application includes a method of vegetatively propagating a plant of a tobacco cultivar comprising the steps of (a) collecting tissue capable of being propagated from a plant of a tobacco cultivar dS1564 or dS1564MS; (b) cultivating the tissue to obtain a proliferated shoot; and (c) rooting the proliferated shoots to obtain a rooted plantlet.

In an aspect, the present application includes a method of vegetatively propagating a plant of a tobacco cultivar comprising the steps of (a) collecting tissue capable of being propagated from a plant of a tobacco cultivar dS1564 or dS1564MS; (b) cultivating the tissue to obtain a proliferated shoot; (c) rooting the proliferated shoots to obtain a rooted plantlet; and (d) growing a plant from the rooted plantlet.

In an aspect, the present application includes a method of introducing a desired trait into a tobacco cultivar comprising: (a) crossing a plant of a first tobacco cultivar dS1564 or dS1564MS, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar; and (e) repeating steps (c) and (d) three or more times (e.g., 3, 4, 5, 6, 7, 8, 9, 10, and the like) in succession to produce selected fourth or higher backcross progeny that comprise the desired trait. In an aspect, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present application includes a method of introducing a desired trait into a tobacco cultivar comprising: (a) crossing a plant of a first tobacco cultivar dS1564, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar dS1564; and (e) repeating steps (c) and (d) three or more times in succession to produce selected fourth or higher backcross progeny that comprise the desired trait, where the trait is cytoplasmic male sterility (CMS). In an aspect, steps (c) and (d) can be repeated one or more times in succession to produce second or higher backcross progeny comprising the desired trait, where the trait is CMS.

In an aspect, the present application includes a method of introducing a desired trait into a tobacco cultivar comprising: (a) crossing a plant of a first tobacco cultivar dS1564, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar to produce a backcross $BC_1F_1$ progeny seed; (d) growing the $BC_1F_1$ progeny seed and selecting a backcross $BC_1F_1$ progeny plant comprising the desired trait and the physiological and essentially all of morphological characteristics of the first tobacco cultivar; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In an aspect, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present application includes a method of introducing a desired trait into a tobacco cultivar comprising: (a) crossing a plant of a first tobacco cultivar dS1564 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar, dS1564 to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar dS1564; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is dS1564MS. In an aspect, steps (c) and (d) can be repeated one or more times in succession to produce second or higher backcross progeny comprising the desired trait, where the trait is CMS and the CMS trait is obtained from the cytoplasm of *Nicotiana suaveolens*.

In an aspect, the present application includes a tobacco plant produced by a method comprising introducing a desired trait into a tobacco cultivar comprising: (a) crossing a plant of a first tobacco cultivar dS1564 or dS1564MS, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar dS1564 or dS1564MS to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar dS1564 or dS1564MS; and (e) repeating steps (c) and (d) three or more times in succession to produce selected fourth or higher backcross progeny that comprise the desired trait. In an aspect, steps (c) and (d) can be repeated one or more times in succession to produce second or higher backcross progeny that comprise the desired trait.

In another aspect, the present application includes a method of introducing a desired trait into a tobacco cultivar comprising: (a) crossing a plant of a first tobacco cultivar dS1564 or dS1564MS with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar dS1564 or dS1564MS to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, dS1564 or dS1564MS; and (e) repeating steps (c) and (d) one or more times in succession to produce a selected second, third, fourth or higher backcross progeny plant that comprises the desired trait and essentially all of the physiological and morphological characteristics of the first tobacco cultivar, dS1564 or dS1564MS.

In another aspect, the present application includes a method of introducing a desired trait into a tobacco cultivar comprising: (a) crossing a plant of a first tobacco cultivar dS1564 or dS1564MS, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an F1 progeny seed; (b) growing the F1 progeny seed into an F1 progeny plant and selecting the F1 progeny plant having the desired trait; (c) crossing the selected F1 progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, dS1564 or dS1564MS; and (e) repeating steps (c) and (d) one or more times in succession to produce a selected second, third, fourth or higher backcross progeny plant that comprises the desired trait and essentially all of the physiological and morphological characteristics of the first tobacco cultivar, dS1564 or dS1564MS.

In another aspect, the present application includes a method of introducing a desired trait into a tobacco cultivar comprising: (a) crossing a plant of a first tobacco cultivar dS1564 or dS1564MS, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an F1 progeny seed; (b) growing the F1 progeny seed into an F1 progeny plant and selecting the F1 progeny plant having the desired trait; (c) crossing the selected F1 progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, dS1564 or dS1564MS; and (e) repeating steps (c) and (d) one or more times in succession to produce a selected second, third, fourth or higher backcross progeny plant that comprises the desired trait and essentially all of the physiological and morphological characteristics of the first tobacco cultivar, dS1564 or dS1564MS, where the plant has a desired trait of disease resistance.

In another aspect, the present application includes a method for producing a tobacco plant comprising: identifying a first tobacco plant comprising a nucleotide sequence selected from the group consisting of SEQ ID NOs: 6 to 10, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence. In an aspect, the second tobacco plant comprises a nucleotide sequence selected from the group consisting of SEQ ID NOs: 6 to 10, and any combination thereof. In a further aspect, the third tobacco plant comprises a nucleotide sequence selected from the group consisting of SEQ ID NOs: 6 to 10, and any combination thereof. In an aspect, the first tobacco plant is a plant of tobacco cultivar dS1564 or dS1564MS. In another aspect, the second tobacco plant is a plant of tobacco cultivar dS1564 or dS1564MS. In a further aspect, the third tobacco plant is a plant of tobacco cultivar dS1564 or dS1564MS.

In another aspect, the present application includes a method of producing a plant of tobacco cultivar dS1564 or dS1564MS comprising at least one (e.g., 1, 2, 3, 4, 5, 6, 7, 8, and the like) additional desired trait comprising the steps of: (a) collecting tissue capable of being propagated from a plant of tobacco cultivar dS1564 or dS1564MS; and (b) introducing at least one transgene (nucleic acid construct) conferring at least one desired trait into the tissue.

In another aspect, the present application includes a method of producing an herbicide resistant tobacco plant comprising transforming a tobacco plant, or part thereof, produced by growing a seed of tobacco cultivar dS1564 or dS1564MS with at least one transgene (nucleic acid construct), where the at least one transgene (nucleic acid construct) confers resistance to an herbicide. In a further aspect, an herbicide is selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present application includes an herbicide resistant tobacco plant produced by a method comprising transforming a tobacco plant, or part thereof, produced by growing a seed of tobacco cultivar dS1564 or dS1564MS with at least one transgene (nucleic acid construct), where the at least one transgene (nucleic acid construct) confers resistance to an herbicide. In a further aspect, an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present application includes a method of producing a pest and/or insect resistant tobacco plant where the method comprises transforming a tobacco plant produced by growing a seed of tobacco cultivar dS1564 or dS1564MS, with at least one transgene (nucleic acid construct) that confers pest and/or insect resistance.

In a further aspect, the present application includes a pest and/or insect resistant tobacco plant produced by a method comprising transforming a tobacco plant produced by growing a seed of tobacco cultivar dS1564 or dS1564MS, with at least one transgene (nucleic acid construct) that confers pest and/or insect resistance.

In a further aspect, the present application includes a pest and/or insect resistant tobacco plant produced by a method comprising transforming a tobacco plant produced by growing a seed of tobacco cultivar dS1564 or dS1564MS, with at least one transgene (nucleic acid construct) that confers pest and/or insect resistance, where the transgene (nucleic acid construct) encodes a *Bacillus thuringiensis* (BT) endotoxin.

In another aspect, the present application includes a method of producing a disease resistant tobacco plant, the method comprising transforming a tobacco plant produced by growing a seed of tobacco cultivar dS1564 or dS1564MS with at least one transgene (nucleic acid construct) that confers disease resistance.

In a further aspect, the present application includes a disease resistant tobacco plant produced by transforming a tobacco plant produced by growing a seed of tobacco cultivar dS1564 or dS1564MS with at least one transgene (nucleic acid construct) that confers disease resistance.

dS1564

In an aspect, the present application provides tobacco cultivars, and parts thereof, grown or developed from dS1564. In another aspect, the present application provides a tobacco plant, or part thereof, produced by growing a seed of dS1564. In a further aspect, a plant of the present application can include a plant with all, or essentially all, of the morphological and physiological characteristics of cultivar dS1564.

While not being limited by process, dS1564 is an inbreeding-derived version of flue-cured tobacco cultivar K326 carrying homozygous introgressions at two loci (nic1 and nic2 loci), which introgressions result in an overall reduction of alkaloid content in the line. dS1564 progeny plants have genetic backgrounds that are at least 55%, at least 65%, at least 75%, at least 85%, at least 90%, at least 95%, at least 97%, at least 98%, or at least 99% similar to K326. dS1564 plants exhibit low nicotine levels.

dS1564MS

In an aspect, the present application provides tobacco cultivars, and parts thereof, grown or developed from dS1564MS. In a further aspect, the present application also includes a tobacco plant, or part thereof, produced by growing a seed of dS1564MS. In a still further aspect, a plant of the present application can include a plant with all, or essentially all, of the morphological and physiological characteristics of cultivar dS1564MS. dS1564MS is a male-sterile (MS) version of dS1564. Because the dS1564MS line is male sterile, it is maintained via pollination with dS1564. dS1564 is crossed as the male parent to dS1564MS to prepare dS1564MS $F_1$ progeny plants. dS1564MS progeny plants can have genetic backgrounds that are at least 55%, at least 65%, at least 75%, at least 85%, at least 90%, at least 95%, at least 97%, at least 98%, or at least 99% similar to K326. dS1564MS and dS1564MS $F_1$ progeny plants exhibit low nicotine levels.

Other Plants

The present application includes a tobacco seed produced by crossing two parent tobacco plants and harvesting the resultant tobacco seed, where at least one parent tobacco plant is dS1564. In one aspect, the dS1564 is the male parent plant. In another aspect, the dS1564MS is the female parent plant. One aspect of the present application provides tobacco plants that are homozygous at the nic1 and nic2 loci, and which share a genetic background that is greater than about 75%, 80%, 85%, 90%, 95%, 98%, or 99% similar to K326 or MS K326 (male sterile K326). In one aspect, approximately or greater than about 50%, 75%, or 100% of a progeny's genetics is provided by a plant of the present application that is homozygous at the nic1 and nic2 loci. In one aspect, a plant of the present application has a genetic background that is at least 95%, at least 97%, at least 98%, or at least 99% similar to K326 or MS K326. In another aspect, a plant of the present application exhibits low nicotine. In one aspect, a plant of the present application is the progeny plant of a female or male parent plant that is *Fusarium* wilt resistant. In another aspect, a plant of dS1564 has low resistance to black shank and moderate resistance to bacterial wilt.

Thus, in an aspect, the present application provides a cured tobacco comprising the leaves of the tobacco plant designated dS1564. In another aspect, the present application provides a cured tobacco comprising the leaves of the tobacco plant designated dS1564MS.

In an aspect, the present application provides a cured tobacco comprising the stems of the tobacco plant designated dS1564. In another aspect, the present application provides a cured tobacco comprising the stems of the tobacco plant designated dS1564MS.

In an aspect, the present application provides a cured tobacco comprising the leaves and stems of the tobacco plants designated dS1564. In another aspect, the present application provides a cured tobacco comprising the leaves and stems of the tobacco plants designated dS1564MS.

The present application also provides a container of dS1564 or dS1564MS seeds or other seeds of the present application in which alkaloids obtained from tobacco plants grown from greater than about 50% of the seeds have decreased nicotine. In another aspect, alkaloids obtained from dS1564 or dS1564MS plants or other plants of the present application grown from greater than about 55%, 60%, 65%, 70%, 75%, 80%, 85%, 90%, or 95% of the seeds in the container have decreased nicotine.

The container of dS1564 or dS1564MS seeds or other seeds of the present application may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds.

Containers of dS1564 or dS1564MS seeds or other seeds of the present application may be any container available in the art. By way of a non-limiting example, a container may be a box, a bag, a packet, a pouch, a tape roll, a pail, a foil, or a tube.

In another aspect, the present application also provides a container of dS1564 or dS1564MS in which greater than about 50% of dS1564 or dS1564MS seeds or other seeds of the present application have decreased nicotine.

Tobacco material obtained from the tobacco lines, varieties or hybrids of the present application can be used to make tobacco products including, without limitation, cigarette products (e.g., cigarettes and bidi cigarettes), cigar products (e.g., cigar wrapping tobacco and cigarillos), pipe tobacco products, smokeless cigarette products, smokeless tobacco products (e.g., moist snuff, dry snuff, and chewing tobacco), films, chewables, tabs, shaped parts, gels, consumable units, insoluble matrices, hollow shapes and the like. See, e.g., U.S. Patent Publication No. US 2006/0191548, which is herein incorporated by reference in its entirety.

Tobacco products derived from plants of the present application also include cigarettes and other smoking articles, particularly those smoking articles including filter elements, wherein the rod of smokeable material includes cured tobacco within a tobacco blend. In an aspect, a tobacco product can include but is not limited to pipe tobacco, cigar tobacco, cigarette tobacco, chewing tobacco, leaf tobacco, shredded tobacco, and/or cut tobacco or any combination thereof.

In an aspect, the tobacco product of the present application can be a blended tobacco product. In another aspect of the application, the tobacco product of the present application can be a reduced nicotine tobacco product. In still another aspect, the tobacco product of the present application can be a blended tobacco product with reduced nicotine content. Thus, the tobacco product of the present application can be a blended reduced nicotine tobacco product. Tobacco product material comprises a blend of tobacco materials from the present application, wherein the blend comprises at least about 5, 10, 20, 30, 40, 50, 60, 70, 80, 90, or 95 percent by weight of a cured tobacco, or any range therein, based on the dry weight of the tobacco material. US 2008/0245377 is herein incorporated by reference for blend mixtures in its entirety.

In an aspect, tobacco products having a reduced amount of nicotine can be manufactured using tobacco plant material from plants and plant parts of the present application. Thus, in an aspect, a tobacco product manufactured using tobacco plant material from plants and plant parts of the present application can comprise a reduced amount of nicotine or total alkaloid selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.04%, less than 0.03%, less than 0.02%, less than 0.01%, less than 0.005%, less than 0.025%, less than 0.001%, and less than 0.0005%. In another aspect, a tobacco product manufactured using tobacco plant material from plants and plant parts of the present application can comprises a nicotine or total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.04%, less than 0.03%, less than 0.02%, less than 0.01%, less than 0.005%, less than 0.025%, less than 0.001%, and less than 0.0005%.

Unless specified otherwise, measurements of alkaloid or nicotine levels (or another leaf chemistry or property characterization) or leaf grade index values mentioned herein for a tobacco plant, variety, cultivar, or line refer to average measurements, including, for example, an average of multiple leaves of a single plant or an average measurement from a population of tobacco plants from a single variety, cultivar, or line. In an aspect, the nicotine or alkaloid level (or another leaf chemistry or property characterization) of a tobacco plant is measured after topping in a pooled leaf sample collected from leaf number 3, 4, and 5 after topping. In another aspect, the nicotine or alkaloid level (or another leaf chemistry or property characterization) of a tobacco plant is measured after topping in a leaf having the highest level of nicotine or alkaloid (or another leaf chemistry or property characterization). In an aspect, the nicotine or alkaloid level of a tobacco plant is measured after topping in leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In another aspect, the nicotine or alkaloid level (or another leaf chemistry or property characterization) of a tobacco plant is measured after topping in a pool of two or more leaves with consecutive leaf numbers selected from the group consisting of leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. In another aspect, the nicotine or alkaloid level (or another leaf chemistry or property characterization) of a tobacco plant is measured after topping in a leaf with a leaf number selected from the group consisting of between 1 and 5, between 6 and 10, between 11 and 15, between 16 and 20, between 21 and 25, and between 26 and 30. In another aspect, the nicotine or alkaloid level (or another leaf chemistry or property characterization) of a tobacco plant is measured after topping in a pool of two or more leaves with leaf numbers selected from the group consisting of between 1 and 5, between 6 and 10, between 11 and 15, between 16 and 20, between 21 and 25, and between 26 and 30. In another aspect, the nicotine or alkaloid level (or another leaf chemistry or property characterization) of a tobacco plant is measured after topping in a pool of three or more leaves with leaf numbers selected from the group consisting of between 1 and 5, between 6 and 10, between 11 and 15, between 16 and 20, between 21 and 25, and between 26 and 30.

As used herein, leaf numbering is based on the leaf position on a tobacco stalk with leaf number 1 being the youngest leaf (at the top) after topping and the highest leaf number assigned to the oldest leaf (at the bottom).

A population of tobacco plants or a collection of tobacco leaves for determining an average measurement (e.g., alkaloid or nicotine level or leaf grading) can be of any size, for example, 5, 10, 15, 20, 25, 30, 35, 40, or 50. Industry-accepted standard protocols are followed for determining average measurements or grad index values.

As used herein, "topping" refers to the removal of the stalk apex, including the SAM, flowers, and up to several adjacent leaves, when a tobacco plant is near vegetative maturity and around the start of reproductive growth. Typically, tobacco plants are topped in the button stage (soon after the flower begins to appear). For example, greenhouse or field-grown tobacco plants can be topped when 50% of the plants have at least one open flower. Topping a tobacco plant results in the loss of apical dominance and also induce increased alkaloid production.

Typically, the nicotine or alkaloid level (or another leaf chemistry or property characterization) of a tobacco plant is measured about 2 weeks after topping. Other time points can also be used. In an aspect, the nicotine or alkaloid level (or another leaf chemistry or property characterization) of a tobacco plant is measured about 1, 2, 3, 4, or 5 weeks after topping. In another aspect, the nicotine or alkaloid level (or another leaf chemistry or property characterization) of a tobacco plant is measured about 3, 5, 7, 10, 12, 14, 17, 19, or 21 days after topping.

A tobacco plant of the present application designated dS1746, dS1746MS, dS1564 or dS1564MS can be used in a plant breeding program to create useful lines, cultivars, varieties, progeny, inbreds, and hybrids. Thus, in an aspect, an $F_1$, $F_2$, $F_3$, or later generation tobacco plant containing nic1 and nic2 loci is crossed with a second Nicotiana plant, and progeny of the cross are identified in which the nic1 and nic2 loci are present. It will be appreciated that the second Nicotiana plant can be TN90, K326 or any other Nicotiana species or line, optionally with an additional desirable trait, such as herbicide resistance.

In still another aspect, methods of the present application further include self-pollinating or pollinating a male sterile pollen acceptor with a pollen donor capable of being used in production of a progeny plant of the present application, such as a male sterile hybrid of the present application.

Breeding can be carried out via any known procedures. DNA fingerprinting, SNP or similar technologies may be used in a marker-assisted selection (MAS) breeding program to transfer or breed mutant alleles of a nicotine demethylase gene into other tobaccos. For example, a breeder can create segregating populations from hybridizations of a genotype containing nic1 and nic2 with an agronomically desirable genotype. Plants in the $F_2$ or backcross generations can be screened using a marker (e.g., SNP makers having sequences set forth in SEQ ID Nos: 1 to 5), using one of the techniques known in the art or disclosed herein. Plants identified as possessing one or both of nic1 and nic2 can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered. A recurrent parent in the present application can be dS1746, dS1746MS, dS1564 or dS1564MS. Other breeding techniques can be found, for example, in Wernsman, E. A., and Rufty, R. C., 1987. Chapter Seventeen. Tobacco. pages 669-698 In: Cultivar Development. Crop Species. W. H. Fehr (ed.), MacMillan Publishing Go., Inc., New York, N.Y., incorporated herein by reference in their entireties.

Nicotiana species which exhibit breeding compatibility with Nicotiana tabacum include Nicotiana amplexicaulis, PI 271989; Nicotiana benthamiana PI 555478; Nicotiana bigelovii PI 555485; Nicotiana debneyi; Nicotiana excelsior PI 224063; Nicotiana glutinosa PI 555507; Nicotiana goodspeedii PI 241012; Nicotiana gossei PI 230953; Nicotiana hesperis PI 271991; Nicotiana knightiana PI 555527; Nicotiana maritima PI 555535; Nicotiana megalosiphon PI 555536; Nicotiana nudicaulis PI 555540; Nicotiana paniculata PI 555545; Nicotiana plumbaginifolia PI 555548; Nicotiana repanda PI 555552; Nicotiana rustica; Nicotiana suaveolens PI 230960; Nicotiana sylvestris PI 555569; Nicotiana tomentosa PI 266379; Nicotiana tomentosiformis; and Nicotiana trigonophylla PI 555572. See also, Compendium of Tobacco Diseases published by American Phytopathology Society, or The Genus Nicotiana Illustrated, published by Japan Tobacco Inc, hereby incorporated by reference in their entireties.

The result of a plant breeding program using the mutant tobacco plants described herein includes useful lines, cultivars, varieties, progeny, inbreds, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972, on Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A "line" as distinguished from a variety most often denotes a group of plants used non-commercially, for example in plant research. A line typically displays little overall variation between individuals for one or more traits of interest, although there may be some variation between individuals for other traits.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In an aspect in which the female parent plants are CMS, pollen may be harvested from male fertile plants and applied manually to the stigmas of CMS female parent plants, and the resulting $F_1$ seed is harvested.

Plants can be used to form single-cross tobacco $F_1$ hybrids. In such an aspect, the plants of the parent varieties can be grown as substantially homogeneous adjoining populations to facilitate natural cross-pollination from the male parent plants to the female parent plants. The $F_1$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, threeway crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Successful crosses yield $F_1$ plants that are fertile, have nic1 and nic2, and can be backcrossed with one of the parents, such as dS1746, dS1746MS, dS1564 or dS1564MS, if desired. In an aspect, a plant population in the $F_2$ generation is screened for nic1 and nic2. Selected plants can be crossed with one of the parents and the first backcross ($BC_1$) generation plants are self-pollinated to produce a $BC_1F_2$ population that is again screened for nic1 and nic2. The process of backcrossing, self-pollination, and screening is repeated, for example, at least four times, until the final screening produces a plant that is fertile and reasonably similar to the recurrent parent. This plant, if desired, is self-pollinated and the progeny are subsequently screened again to confirm that the plant exhibits the same low nicotine phenotype as dS1746, dS1746MS, dS1564 or dS1564MS. Breeder's seed of the selected plant is produced using standard methods including, for example, field testing, confirmation of nic1 and nic2 genotype, chemical analyses of cured leaf to determine the level of alkaloids or nicotine.

In one aspect, a $F_1$ progeny is the result of a cross between dS1746 and dS1746MS (or between dS1564 and dS1564MS) to generate $F_1$ progeny that are male sterile. Male sterile tobacco plants may be produced by any method known in the art. Methods of producing male sterile tobacco are described in Wernsman, E. A., and Rufty, R. C., 1987. Chapter Seventeen. Tobacco. pages 669-698 In: Cultivar Development. Crop Species. W. H. Fehr (ed.), MacMillan Publishing Go., Inc., New York, N.Y. 761 pp.

The present application further provides methods of producing a tobacco plant by crossing one of cultivars dS1746 or dS1746MS with itself or a different tobacco line. The application further relates to methods for producing other tobacco cultivars or breeding lines derived from cultivars dS1746 or dS1746MS by crossing a plant of cultivars dS1746 or dS1746MS with a second tobacco plant and growing the progeny seed to yield a dS1746 or dS1746MS-derived tobacco plant. An additional aspect of the present application provides a method for producing a tobacco plant that contains in its genetic material one or more transgenes, comprising crossing cultivars of the present application with a second cultivar containing one or more transgenes wherein progeny are produced, so that the genetic material of the progeny that result from the cross comprise the transgene(s) optionally operably linked to one or more regulatory elements. In one aspect, the second cultivar may be a plant derived from cultivars dS1746 or dS1746MS transformed with one or more transgenes.

The application further provides for the vegetative propagation of a plant of cultivar dS1746 or dS1746MS hybrids and progeny thereof. In one aspect, the application provides for a method of vegetatively propagating a plant of a tobacco cultivar comprising collecting tissue capable of being propagated from a plant of cultivar dS1746 or dS1746MS, cultivating the tissue to obtain a proliferated shoot and rooting the proliferated shoots to obtain a rooted plantlet. In another aspect, the plant tissue may be collected from an $F_1$ hybrid of a plant of cultivar dS1746 or dS1746MS. In an aspect, the plant tissue may be collected from an $F_2$, $F_3$, $F_4$ or later progeny plant obtained by breeding a plant of cultivar dS1746 or dS1746MS.

The present application further provides methods of producing a tobacco plant by crossing one of cultivars dS1564 or dS1564MS with itself or a different tobacco line. The application further relates to methods for producing other tobacco cultivars or breeding lines derived from cultivars dS1564 or dS1564MS by crossing a plant of cultivars dS1564 or dS1564MS with a second tobacco plant and growing the progeny seed to yield a dS1564 or dS1564MS-derived tobacco plant. An additional aspect of the present application provides a method for producing a tobacco plant that contains in its genetic material one or more transgenes, comprising crossing cultivars of the present application with a second cultivar containing one or more transgenes wherein progeny are produced, so that the genetic material of the progeny that result from the cross comprise the transgene(s) optionally operably linked to one or more regulatory elements. In one aspect, the second cultivar may be a plant derived from cultivars dS1564 or dS1564MS transformed with one or more transgenes.

The application further provides for the vegetative propagation of a plant of cultivar dS1564 or dS1564MS hybrids and progeny thereof. In one aspect, the application provides for a method of vegetatively propagating a plant of a tobacco cultivar comprising collecting tissue capable of being propagated from a plant of cultivar dS1564 or dS1564MS, cultivating the tissue to obtain a proliferated shoot and rooting the proliferated shoots to obtain a rooted plantlet. In another aspect, the plant tissue may be collected from an $F_1$ hybrid of a plant of cultivar dS1564 or dS1564MS. In an aspect, the plant tissue may be collected from an $F_2$, $F_3$, $F_4$ or later progeny plant obtained by breeding a plant of cultivar dS1564 or dS1564MS.

In an aspect, a plant of cultivar dS1746, dS1746MS, dS1564 or dS1564MS is further modified to comprise a mutation in a gene of interest. A plant comprising a mutation in a gene of interest can be identified by selecting or screening mutagenized plant material, or progeny thereof. Such screening and selection methodologies are known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In another aspect, a tobacco plant provided here (e.g., dS1746, dS1746MS, dS1564 or dS1564MS) is subject to further genome editing via one or more precise genome engineering technologies, for example, Transcription activator-like effector nucleases (TALENs), meganuclease, zinc finger nuclease (ZFN), and a clustered regularly-interspaced short palindromic repeats (CRISPR)/Cas9 system, a CRISPR/Cpf1 system, a CRISPR/Csm1 system, and a combination thereof (see, for example, U.S. Patent Application publication 2017/0233756). See, e.g., Gaj et al., *Trends in Biotechnology*, 31(7):397-405 (2013). In an aspect, a tobacco plant or plant genome provided herein is mutated or edited by a nuclease selected from the group consisting of a meganuclease, a ZFN, a TALEN, a CRISPR/Cas9 nuclease, a CRISPR/Cpf1 nuclease, or a CRISPR/Csm1 nuclease.

It is understood that a tobacco plant of the present application, including dS1746, dS1746MS, dS1564 or dS1564MS, can be transformed by a genetic construct (nucleic acid construct) or transgene using any technique known in the art. Without limitation, an example of a desired trait can include herbicide resistance, pest resistance, disease resistance, high yield, high grade index, curability, curing quality, mechanical harvestability, holding ability, leaf quality, height, plant maturation (e.g., early maturing, early to medium maturing, medium maturing, medium to late maturing, or late maturing), stalk size (e.g., small, medium, or large stalk), or leaf number per plant (e.g., small (e.g., 5-10 leaves), medium (e.g., 11-15 leaves), or large (e.g., 16-21) number of leaves), or any combination. Any plant of the present application can be used as a basis for tissue culture, regeneration, transformed, or a combination of any of these. In an aspect, a plant of the present application derived by tissue culture, transformation, or both has all, or essentially all, of the morphological and physiological characteristics of cultivar dS1746 or dS1746MS.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In an aspect, green leaf tobacco provided can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, e.g., U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cure, aged, and fermented tobacco can be further processed (e.g., cut, shredded, expanded, or blended). See, for example, U.S. Pat. Nos. 4,528,993; 4,660,577; and 4,987,907. In an aspect, the cured tobacco material of the present disclosure is sun-cured. In another aspect, the cured tobacco material of the present disclosure is flue-cured, air-cured, or fire-cured.

Tobacco material obtained from the tobacco lines, varieties or hybrids of the present disclosure can be used to make tobacco products. As used herein, "tobacco product" is defined as any product made or derived from tobacco that is intended for human use or consumption.

Tobacco products provided include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

In an aspect, a tobacco product of the present disclosure can be a blended tobacco product. In another aspect, a tobacco product of the present disclosure can be a low nicotine tobacco product. In a further aspect, a tobacco product of the present disclosure may comprise nornicotine at a level of less than about 3 mg/g. For example, the nornicotine content in such a product can be 3.0 mg/g, 2.5 mg/g, 2.0 mg/g, 1.5 mg/g, 1.0 mg/g, 750 µg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable.

In an aspect, cured tobacco material or tobacco products provided comprise an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In an aspect, cured tobacco material or tobacco products provided comprise an average nicotine or total alkaloid level less than a level selected from the group consisting of 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, cured tobacco material or tobacco products provided comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, cured tobacco material or tobacco products provided comprise an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

Having now generally described the application, the same will be more readily understood through reference to the following examples that are provided by way of illustration, and are not intended to be limiting of the present application, unless specified.

EXAMPLES

Example 1: Breeding of Homozygous Nic1/Nic2 Low Alkaloid Loci into the TN 90 Background Line dS1746 is a backcross-derived version of burley tobacco cultivar TN 90 carrying homozygous introgressions at two loci (nic1 and nic2 loci), which introgressions result in an overall reduction of alkaloid content in the line. To prepare dS1746, an individual plant grown from a commercial seedlot of TN 90 is selected and initially crossed with a plant grown from the USDA germplasm seedlot of LA Burley 21, a tobacco cultivar homozygous for the nic1 and nic2 loci. A plurality of $F_1$ plants are screened for the presence of the nic1 and nic2 loci utilizing the KASP assays listed in Table 1. Individual $F_1$ plants are selected and backcrossed to TN 90 in a greenhouse to produce $BC_1F_1$ progeny. A plurality of $BC_1F_1$ progeny are screened and an individual plant heterozygous for the nic1 and nic2 loci is identified. Whole genome SNP profiling utilizing a 175K SNP Axiome array is used to select the plant which has both the heterozygous loci and the highest recovery of genome material from the TN90 parent. The selected heterozygous $BC_1F_1$ plant is backcrossed to TN 90 in a greenhouse to produce $BC_2F_1$ seed. Using this backcross procedure, individual heterozygous plants having the nic1 and nic2 loci are identified in the $BC_2F_1$ and $BC_3F_1$ generations.

To produce plants homozygous for the nic1 and nic2 loci, $BC_3F_1$ progeny plants are screened for the loci to identify heterozygous plants. Individual plants heterozygous for the nic1 and nic2 loci are self-pollinated to produce $BC_3F_2$ seed. A plurality of $BC_3F_2$ progeny are genotyped to identify individuals homozygous for the nic1 and nic2 loci. Individual plants homozygous for the nic1 and nic2 loci are self-pollinated to produce $BC_3F_3$ seed. Using this self-pollinating procedure (inbreeding), plants are selected in the $BC_3F_3$ and $BC_3F_4$ generations to produce variety dS1746 which is homozygous for the nic1 and nic2 loci and having greater than 94% of the genome originating from the elite cultivar TN90.

TABLE 1

KASP Assays used for genotyping and selection of nic1 and nic2 loci

| | | | SEQ ID No. | |
|---|---|---|---|---|
| SNP ID | Locus | Marker Sequence (SEQ ID No.) | Low-alkaloid Allele | High-alkaloid Allele |
| Altria_N1_SNP17 | Nic1 | 1 | 6 | 11 |
| Altria_N1_SNP18 | Nic1 | 2 | 7 | 12 |
| Altria_N2_SNP18 | Nic2 | 3 | 8 | 13 |
| Altria_N1_SNP1 | Nic1 | 4 | 9 | 14 |
| Altria_N2_SNP8 | Nic2 | 5 | 10 | 15 |

Example 2: Preparation of Male Sterile Lines

To prepare a male sterile (MS) line, a progeny plant of the $BC_3F_4$ prepared in Example 1 (described above) that is homozygous for the nic1 and nic2 loci is selected and crossed as the male parent to a MS TN 90. The MS $F_1$ progeny plants of the $BC_3F_4 \times MS$ TN 90 cross are male sterile. These MS $F_1$ progeny plants (e.g., $BC_4F_1$ MS) are screened for the nic1 and nic2 loci. Similarly, the $BC_3F_1$ is crossed with a TN 90 to yield a fertile $BC_4F_1$ plant that is screened for the loci. The MS $F_1$ progeny plant, identified as having the loci, is the female parent in a subsequent cross with the fertile male parent $BC_3F_4$, which also has the loci. Progeny of this cross (e.g., MS $F_2$ progeny) are male sterile and those that are homozygous for the nic1 and nic2 loci are identified by genotyping and designated as dS1746MS. To maintain the male sterile line, dS1746MS plants are pollinated with a fertile dS1746 plant.

Example 3: Field Testing of dS1746

Plants from the dS1746 line are grown in a randomized complete block design with three to four replications for evaluation of cured leaf chemistry, yield, and physical quality at a Blackstone field research location and a Chilean nursery at Rancagua during the 2017 and 2018 seasons. Each replicated block in Blackstone is a one-row plot with 25 plants per plot. Each replicated block in Rancagua is a 2-row plot with 100 plants per plot. Plants are stalk cut at maturity, air cured and evaluated by a former USDA tobacco grader. Plot weights are used to determine per acre yields. The fourth leaf counting from the top of twelve different test plants of the air cured varieties are collected after curing to prepare a fifty gram composite leaf sample from each plot. Composite samples are analyzed for percent nicotine, nornicotine, anatabine, and anabasine by gas chromatography. Alkaloid measurement data are shown as the mean of four replicates (Table 2A).

Agronomic measurements are taken on 5 consecutive plants pre replicate. No end plants are included. Measurements are taken just before harvesting and include: plant height, leaf count (after topping), leaf width and length (5th leaf, top down, just before first harvest) and days to 50% flowering (Tables 2B to 2D). The measurements of the five consecutive plants per replicate are then averaged.

TABLE 2A

Alkaloid levels in dS1746 and control plants.

| Variety | Alkaloids (%, percent dry weight) | | | | |
|---|---|---|---|---|---|
| | Nicotine | Nornicotine | Anabasine | Anatabine | Total Alks |
| dS1746 | 0.13493 | 0.0092 | 0 | 0.002825 | 0.14695 |
| LA BU21 | 0.15093 | 0.016975 | 0 | 0.00185 | 0.16975 |
| TN90 LC | 4.18805 | 0.106675 | 0.0159 | 0.11885 | 4.429475 |

TABLE 2B

Leaf measurement of dS1746 and control plants.

| | Leaf Measurements: | | |
|---|---|---|---|
| | AVG. Length (cm) | AVG. Width (cm) | Variety |
| Rep. 4 | 69.4 | 24.4 | dS1746 |
| | 70.2 | 24.4 | LA BU21 |
| | 78.2 | 30.6 | TN90 LC |
| Rep. 3 | 65.4 | 21.6 | LA BU21 |
| | 67.4 | 26 | TN90 LC |
| | 64.6 | 20.6 | dS1746 |
| Rep. 2 | 60.6 | 23 | TN90 LC |
| | 67.8 | 22.1 | dS1746 |
| | 62 | 20.2 | LA BU21 |
| Rep. 1 | 66.8 | 23.3 | dS1746 |
| | 66.2 | 22.4 | LA BU21 |
| | 70.1 | 24.7 | TN90 LC |

TABLE 2C

Leaf count of dS1746 and control plants at flowering.

| | Days to Flower: AVG Leaf No. | 61 days after planting Variety |
|---|---|---|
| Rep. 4 | 20 | dS1746 |
| | 20.8 | LA BU21 |
| | 18.6 | TN90 LC |
| Rep. 3 | 21 | LA BU21 |
| | 21 | TN90 LC |
| | 19.25 | dS1746 |
| Rep. 2 | 19.8 | TN90 LC |
| | 20.4 | dS1746 |
| | 21.2 | LA BU21 |
| Rep. 1 | 19.2 | dS1746 |
| | 20 | LA BU21 |
| | 18.8 | TN90 LC |

TABLE 2D

Plant height of dS1746 and control plants.

| | AVG Plant Height (cm) | Variety |
|---|---|---|
| Rep. 4 | 153.2 | dS1746 |
| | 150.8 | LA BU21 |
| | 150 | TN90 LC |
| Rep. 3 | 153.4 | LA BU21 |
| | 154.8 | TN90 |
| | 151.2 | dS1746 |
| Rep. 2 | 149.4 | TN90 LC |
| | 151.8 | dS1746 |
| | 153.8 | LA BU21 |
| Rep. 1 | 150.6 | dS1746 |
| | 152.4 | LA BU21 |
| | 149.4 | TN90 LC |

Example 4: Breeding of Homozygous Nic1/Nic2 Low Alkaloid Loci into the K326 Background Line dS1564 is an inbreeding-derived version of flue-cured tobacco cultivar K326 carrying two introgressed loci (nic1 and nic2 loci) that result in an overall reduction of alkaloid content in the plant. To prepare dS1564, an individual plant grown from a commercial seedlot of K326 is selected and initially crossed with a plant grown from the USDA germplasm seedlot of LAFC53, a tobacco cultivar homozygous for the nic1 and nic2 loci. A plurality of $F_1$ plants are screened for the presence of the nic1 and nic2 loci. Individual $F_1$ plants are selected and self-pollinated to produce $F_2$ progeny plants. A plurality of $F_2$ progeny plants are screened and an individual plant homozygous for the nic1 and nic2 loci is identified. Whole genome SNP profiling utilizing a 175K SNP Axiome array is used to select the plant which has homozygous nic1 and nic2 loci and the highest recovery of genetic material from the K326 parent. This selected individual is self-pollinated to produce $F_3$ progeny. Using this inbreeding procedure, individual plants homozygous for the nic1 and nic2 loci are identified in the $F_4$ generation to produce $F_5$ seed (designated as line dS1564) which is homozygous for the nic1 and nic2 loci and having greater than 42% of the genetic material originating from the elite cultivar K326. A male sterile version of line dS1564 (designated as "dS1564MS") is also developed.

Example 5: Field Testing of dS1564

Plants from the dS1564 line are grown in a randomized complete block design with three to four replications for evaluation of cured leaf chemistry, yield, and physical quality at a Blackstone field research location and a Chilean nursery at Rancagua during the 2017 and 2018 seasons. Each replicated block in Blackstone is a one-row plot with 25 plants per plot. Each replicated block in Rancagua is a 2-row plot with 100 plants per plot. Plants are stalk cut at maturity, cured and evaluated by a former USDA tobacco grader. Flue cured varieties are to be primed and to be cured using the flue curing barns. Racks are filled completely and uniformly (approximately 45-50 KG of green tobacco per rack). Plot weights are used to determine per acre yields. Twelve random leaves from the third priming of the flue cured varieties per plot for each replicate are collected after curing to prepare a fifty gram composite leaf sample from each plot. Composite samples are analyzed for percent nicotine, nornicotine, anatabine, and anabasine by gas chromatography. Alkaloid measurement data are shown as the mean of four replicates (Table 3A).

Agronomic measurements are taken on 5 consecutive plants pre replicate. No end plants are included. Measurements are taken just before harvesting and include: plant height, leaf count (after topping), leaf width and length (5th leaf, top down, just before first harvest) and days to 50% flowering (Tables 3B to 3D). The measurements of the five consecutive plants per replicate are then averaged.

TABLE 3A

Alkaloid levels in dS1564 and control plants.

| | Alkaloids (%, percent dry weight) | | | | |
|---|---|---|---|---|---|
| Variety | Nicotine | Nornicotine | Anabasine | Anatabine | Total Alks |
| dS1564 | 0.10685 | 0.002025 | 0 | 0.001825 | 0.1107 |
| LA FC53 | 0.1566 | 0.00845 | 0 | 0.0046 | 0.16965 |
| K326 | 1.51663 | 0.037975 | 0.005575 | 0.045325 | 1.6055 |

TABLE 3B

Leaf measurement of dS1564 and control plants.

| | Leaf Measurements: | | |
|---|---|---|---|
| | AVG Length (cm) | AVG Width (cm) | Variety |
| Rep. 4 | 62.4 | 25 | K326 |
| | 63.8 | 27.2 | dS1564 |
| | 59.4 | 26 | LA FC53 |
| Rep. 3 | 59.2 | 25.2 | LA FC53 |
| | 60.6 | 23.8 | K326 |
| | 61.2 | 25 | dS1564 |
| Rep. 2 | 57.8 | 23 | LA FC53 |
| | 60.2 | 26.6 | dS1564 |
| | 61.4 | 24.4 | K326 |
| Rep. 1 | 62.4 | 29 | dS1564 |
| | 62.8 | 24 | K326 |
| | 53.2 | 22 | LA FC53 |

TABLE 3B

Leaf count of dS1564 and control plants at flowering.

| | Days to Flower: AVG Leaf No. | 62 days after planting Variety |
|---|---|---|
| Rep. 4 | 22.8 | K326 |
| | 21 | dS1564 |
| | 20.4 | LA FC53 |
| Rep. 3 | 19.2 | LA FC53 |
| | 23.4 | K326 |
| | 18.8 | dS1564 |
| Rep. 2 | 18.4 | LA FC53 |
| | 18.6 | dS1564 |
| | 21 | K326 |
| Rep. 1 | 17 | dS1564 |
| | 21.2 | K326 |
| | 20.6 | LA FC53 |

TABLE 3D

Plant height of dS1564 and control plants.

| | AVG Height (cm) | Variety |
|---|---|---|
| Rep. 4 | 150.4 | K326 |
| | 151.6 | dS1564 |
| | 148.2 | LA FC53 |
| Rep. 3 | 148.2 | LA FC53 |
| | 148.2 | K326 |
| | 146.8 | dS1564 |
| Rep. 2 | 147.8 | LA FC53 |
| | 148 | dS1564 |
| | 148 | K326 |
| Rep. 1 | 141.4 | dS1564 |
| | 147.6 | K326 |
| | 156.4 | LA FC53 |

DEPOSIT INFORMATION

A deposit of the proprietary inbred plant lines disclosed above and recited in the appended claims have been made with American Type Culture Collection (ATCC), 10801 University Boulevard, Manassas, VA 20110. The date of deposit for dS1746 and dS1564 was Oct. 9, 2018. The date of deposit for dS1746MS and dS1564MS was Nov. 22, 2019. The deposits of 2500 seeds for each variety was taken from the same deposits maintained since prior to the filing date of this application. Upon issuance of a patent, all restrictions upon the deposits will be irreversibly removed, and the deposits are intended to meet all of the requirements of 37 C.F.R. § 1.801-1.809. The ATCC has issued the following accession numbers: ATCC Accession No. PTA-125409 for dS1746, ATCC Accession No. PTA-126414 for dS1746MS, ATCC Accession No. PTA-125408 for dS1564, and ATCC Accession No. PTA-126413 for dS1564MS. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

What is claimed is:

1. A method for producing a tobacco seed, the method comprising the steps of:
    crossing two tobacco plants, wherein at least one of the two tobacco plants is a tobacco plant produced by growing a seed of tobacco cultivar dS1746, a representative sample seed of said cultivar dS1746 having been deposited with the ATCC under ATCC Accession No. PTA-125409, and
    harvesting at least one progeny tobacco seed resulting from said crossing.

2. The method of claim 1, further comprising:
    growing a progeny tobacco plant from said progeny tobacco seed, and
    harvesting at least one tobacco leaf from said progeny tobacco plant.

3. A harvested progeny tobacco seed of claim 1.

4. A harvested leaf of the progeny tobacco plant of claim 2.

5. The harvested leaf of claim 4, wherein said leaf comprises a nicotine level of less than 0.2% dry weight.

6. Cured tobacco comprising tobacco material from the harvested leaf of claim 4.

7. A tobacco product comprising the cured tobacco of claim 6, wherein said tobacco product is selected from the group consisting of pipe tobacco, cigar tobacco, cigarette tobacco, chewing tobacco, leaf tobacco, shredded tobacco, and cut tobacco.

8. A tobacco product comprising the cured tobacco of claim 6, wherein said tobacco product is selected from the group consisting of a cigarillo, a non-ventilated recess filter cigarette, a vented recess filter cigarette, a cigar, snuff, and chewing tobacco.

9. The tobacco product of claim 7, wherein said tobacco product has a nicotine level of less than 0.2% dry weight.

10. The tobacco product of claim 8, wherein said tobacco product has a nicotine level of less than 0.2% dry weight.

11. A method for producing a tobacco seed, the method comprising the steps of:
    crossing two tobacco plants wherein at least one of the two tobacco plants is a tobacco plant produced by growing the seed of tobacco cultivar dS1746MS, a representative sample seed of said cultivar dS1746MS having been deposited with the ATCC under ATCC Accession No. PTA-126414, and
    harvesting at least one progeny tobacco seed resulting from said crossing.

12. The method of claim 11, further comprising:
    growing a progeny tobacco plant from said at least one progeny tobacco seed, and
    harvesting at least one tobacco leaf from said progeny tobacco plant.

13. A harvested progeny tobacco seed of claim 11.

14. A harvested leaf of the progeny tobacco plant of claim 12.

15. The harvested leaf of claim 14, wherein said harvested leaf comprises a nicotine level of less than 0.2% dry weight.

16. Cured tobacco comprising tobacco material from the harvested leaf of claim 14.

17. A tobacco product comprising the cured tobacco of claim 16, wherein said tobacco product is selected from the group consisting of pipe tobacco, cigar tobacco, cigarette tobacco, chewing tobacco, leaf tobacco, shredded tobacco, and cut tobacco.

18. A tobacco product comprising the cured tobacco of claim 16, wherein said tobacco product is selected from the group consisting of a cigarillo, a non-ventilated recess filter cigarette, a vented recess filter cigarette, a cigar, snuff, and chewing tobacco.

19. The tobacco product of claim 17, wherein said tobacco product has a nicotine level of less than 0.2% dry weight.

20. The tobacco product of claim 18, wherein said tobacco product has a nicotine level of less than 0.2% dry weight.

\* \* \* \* \*

SEQUENCE LISTING

Sequence total quantity: 15
SEQ ID NO: 1         moltype = DNA   length = 141

| FEATURE | Location/Qualifiers |
|---|---|
| variation | 71 |
| | note = n is a, c, g, or t |
| source | 1..141 |
| | mol_type = genomic DNA |
| | organism = Nicotiana tabacum |

SEQUENCE: 1

```
agaacaaaga gatttcgttt attattatta ttgaaaagta tttgtaagat attatgaggt   60
gtcagatagg natatgatgt aattgggtgt cgcccttgaa gaccgcctac taagttggta  120
atccaaacaa aagtactgtc a                                            141
```

| SEQ ID NO: 2 | moltype = DNA  length = 141 |
|---|---|
| FEATURE | Location/Qualifiers |
| variation | 71 |
| | note = n is a, c, g, or t |
| source | 1..141 |
| | mol_type = genomic DNA |
| | organism = Nicotiana tabacum |

SEQUENCE: 2

```
attttttcct tctagaaaac aaagatccag atcctgatag taaaagtgat atgcctctaa   60
agcacatgtt ngtacaagcc gaccagaaga agtaatcgtc aattaccaga tcctagacac  120
aaacttccta gagctggaga g                                            141
```

| SEQ ID NO: 3 | moltype = DNA  length = 141 |
|---|---|
| FEATURE | Location/Qualifiers |
| variation | 71 |
| | note = n is a, c, g, or t |
| source | 1..141 |
| | mol_type = genomic DNA |
| | organism = Nicotiana tabacum |

SEQUENCE: 3

```
tgtgaaggaa acttaatgac ttgatgtaac atagatggta caacatccat gtcatgaatc   60
catggcctcc naagaatcac attataagtc atgtccgtgt ctattacttg gaatttcgta  120
tccttgataa ctccttctac a                                            141
```

| SEQ ID NO: 4 | moltype = DNA  length = 121 |
|---|---|
| FEATURE | Location/Qualifiers |
| variation | 61 |
| | note = n is a, c, g, or t |
| source | 1..121 |
| | mol_type = genomic DNA |
| | organism = Nicotiana tabacum |

SEQUENCE: 4

```
atcatgtcta attgatttaa ttgctgtatt tgctcaaact gccttatttg gactatgtga   60
nacatgctag gttagaaata tatgttttaa cttggtgtga aatttaattt aattgagtat  120
t                                                                  121
```

| SEQ ID NO: 5 | moltype = DNA  length = 121 |
|---|---|
| FEATURE | Location/Qualifiers |
| variation | 61 |
| | note = n is a, c, g, or t |
| source | 1..121 |
| | mol_type = genomic DNA |
| | organism = Nicotiana tabacum |

SEQUENCE: 5

```
ttacataaat ataaaggttt aattgaaagt tatacttttt ggtcaaacac aaataccgta   60
ncaaaatagt tcgatacggt taggtatttt cttgtttggt tcggtacggc ttcgatatta  120
t                                                                  121
```

| SEQ ID NO: 6 | moltype = DNA  length = 141 |
|---|---|
| FEATURE | Location/Qualifiers |
| source | 1..141 |
| | mol_type = genomic DNA |
| | organism = Nicotiana tabacum |

SEQUENCE: 6

```
agaacaaaga gatttcgttt attattatta ttgaaaagta tttgtaagat attatgaggt   60
gtcagatagg gatatgatgt aattgggtgt cgcccttgaa gaccgcctac taagttggta  120
atccaaacaa aagtactgtc a                                            141
```

| SEQ ID NO: 7 | moltype = DNA  length = 141 |
|---|---|
| FEATURE | Location/Qualifiers |
| source | 1..141 |
| | mol_type = genomic DNA |
| | organism = Nicotiana tabacum |

SEQUENCE: 7

```
attttttcct tctagaaaac aaagatccag atcctgatag taaaagtgat atgcctctaa   60
agcacatgtt tgtacaagcc gaccagaaga agtaatcgtc aattaccaga tcctagacac  120
aaacttccta gagctggaga g                                            141
```

```
SEQ ID NO: 8              moltype = DNA   length = 141
FEATURE                   Location/Qualifiers
source                    1..141
                          mol_type = genomic DNA
                          organism = Nicotiana tabacum
SEQUENCE: 8
tgtgaaggaa acttaatgac ttgatgtaac atagatggta caacatccat gtcatgaatc    60
catggcctcc caagaatcac attataagtc atgtccgtgt ctattacttg gaatttcgta   120
tccttgataa ctccttctac a                                             141

SEQ ID NO: 9              moltype = DNA   length = 121
FEATURE                   Location/Qualifiers
source                    1..121
                          mol_type = genomic DNA
                          organism = Nicotiana tabacum
SEQUENCE: 9
atcatgtcta attgatttaa ttgctgtatt tgctcaaact gccttatttg gactatgtga    60
aacatgctag gttagaaata tatgttttaa cttggtgtga aatttaattt aattgagtat   120
t                                                                   121

SEQ ID NO: 10             moltype = DNA   length = 121
FEATURE                   Location/Qualifiers
source                    1..121
                          mol_type = genomic DNA
                          organism = Nicotiana tabacum
SEQUENCE: 10
ttacataaat ataaggtttt aattgaaagt tatacttttt ggtcaaacac aaataccgta    60
ccaaaatagt tcgatacggt taggtatttt cttgtttggt tcggtacggc ttcgatatta   120
t                                                                   121

SEQ ID NO: 11             moltype = DNA   length = 141
FEATURE                   Location/Qualifiers
source                    1..141
                          mol_type = genomic DNA
                          organism = Nicotiana tabacum
SEQUENCE: 11
agaacaaaga gatttcgttt attattatta ttgaaaagta tttgtaagat attatgaggt    60
gtcagatagg catatgatgt aattgggtgt cgcccttgaa gaccgcctac taagttggta   120
atccaaacaa aagtactgtc a                                             141

SEQ ID NO: 12             moltype = DNA   length = 141
FEATURE                   Location/Qualifiers
source                    1..141
                          mol_type = genomic DNA
                          organism = Nicotiana tabacum
SEQUENCE: 12
atttttcct tctagaaaac aaagatccag atcctgatag taaaagtgat atgcctctaa     60
agcacatgtt agtacaagcc gaccagaaga agtaatcgtc aattaccaga tcctagacac   120
aaacttccta gagctggaga g                                             141

SEQ ID NO: 13             moltype = DNA   length = 141
FEATURE                   Location/Qualifiers
source                    1..141
                          mol_type = genomic DNA
                          organism = Nicotiana tabacum
SEQUENCE: 13
tgtgaaggaa acttaatgac ttgatgtaac atagatggta caacatccat gtcatgaatc    60
catggcctcc taagaatcac attataagtc atgtccgtgt ctattacttg gaatttcgta   120
tccttgataa ctccttctac a                                             141

SEQ ID NO: 14             moltype = DNA   length = 121
FEATURE                   Location/Qualifiers
source                    1..121
                          mol_type = genomic DNA
                          organism = Nicotiana tabacum
SEQUENCE: 14
atcatgtcta attgatttaa ttgctgtatt tgctcaaact gccttatttg gactatgtga    60
cacatgctag gttagaaata tatgttttaa cttggtgtga aatttaattt aattgagtat   120
t                                                                   121

SEQ ID NO: 15             moltype = DNA   length = 121
FEATURE                   Location/Qualifiers
source                    1..121
                          mol_type = genomic DNA
                          organism = Nicotiana tabacum
```

-continued

```
SEQUENCE: 15
ttacataaat ataaaggttt aattgaaagt tatacttttt ggtcaaacac aaataccgta    60
tcaaaatagt tcgatacggt taggtatttt cttgtttggt tcggtacggc ttcgatatta   120
t                                                                  121
```